(12) United States Patent
Lamarche et al.

(10) Patent No.: US 8,183,341 B2
(45) Date of Patent: May 22, 2012

(54) ANTIBACTERIAL COMPOUNDS AND PROCESSES FOR ITS PRODUCTION

(75) Inventors: Matthew J. Lamarche, Cambridge, MA (US); Jennifer A. Leeds, Cambridge, MA (US); Phillipp Krastel, Basel (CH); Hans-Ulrich Naegeli, Basel (CH)

(73) Assignee: Novartis AG, Basel (CH)

( * ) Notice: Subject to any disclaimer, the term of this patent is extended or adjusted under 35 U.S.C. 154(b) by 397 days.

(21) Appl. No.: 12/519,872

(22) PCT Filed: Dec. 19, 2007

(86) PCT No.: PCT/US2007/025955
§ 371 (c)(1),
(2), (4) Date: Jun. 18, 2009

(87) PCT Pub. No.: WO2008/082562
PCT Pub. Date: Jul. 10, 2008

(65) Prior Publication Data
US 2010/0093615 A1    Apr. 15, 2010

Related U.S. Application Data

(60) Provisional application No. 60/871,051, filed on Dec. 20, 2006, provisional application No. 60/889,591, filed on Feb. 13, 2007, provisional application No. 60/892,988, filed on Mar. 5, 2007.

(51) Int. Cl.
*A61K 38/12* (2006.01)
(52) U.S. Cl. ............................. 530/317; 514/2.9; 514/71
(58) Field of Classification Search ........................ None
See application file for complete search history.

(56) References Cited

U.S. PATENT DOCUMENTS

| | | | |
|---|---|---|---|
| 5,139,778 A | 8/1992 | Selva et al. | |
| 5,202,241 A | 4/1993 | Selva et al. | |
| 5,322,777 A | 6/1994 | Selva et al. | |
| 5,514,649 A | 5/1996 | Selva et al. | |
| 5,547,686 A | 8/1996 | Jenkins | |
| 5,599,791 A | * 2/1997 | Tavecchia et al. | ............. 514/2.9 |
| 5,747,295 A | 5/1998 | Selva et al. | |
| 5,843,890 A | 12/1998 | Selva et al. | |
| 5,882,900 A | 3/1999 | Rizzo et al. | |
| 5,891,869 A | 4/1999 | Lociuro et al. | |
| 6,008,225 A | 12/1999 | Lociuro et al. | |
| 6,143,739 A | 11/2000 | Lociuro et al. | |

FOREIGN PATENT DOCUMENTS

| | | |
|---|---|---|
| EP | 0494078 | 7/1992 |
| EP | 0675900 B1 | 12/1998 |
| WO | 96/14427 A1 | 5/1996 |
| WO | 03/105881 A1 | 12/2003 |
| WO | 2006/086012 | 8/2006 |
| WO | 2007/142986 | 12/2007 |

OTHER PUBLICATIONS

Selva et al, "Components of the GE2270 Complex produced by *Planobispora rosea* ATCC53773" Jornal of Antibiotics, Japan Antibiotics Research Association 46(9):1039-1042 (Sep. 1, 1995).
Wieland Brown et al., "Thirteen posttranslational modifications convert a 14-residue peptide into the antibiotic thiocillin," PNAS Early Edition (Feb. 5, 2009) p. 1-5.
Kelly et al, "Thiostrepton Biosynthesis: Prototype for a New Family of bacteriocins." J. Am. Chem. Soc. 131 (12):4327-4334 (2009).
Liao, et al, "Thiopeptide Biosynthesis Featuring Ribosomally Synthesized precursor peptides and Conserved Posttranslational Modifications," Chemistry & Biology 16:141-147 (Feb. 27, 2009).
Tavecchia et al., "Degradation Studies of Antibiotic MDL 62,879 (GE2270A) and Revision of the Structure." Tetrahedron 51(16):4867-4890 (1995).
Selva et al., "Antibiotic GE2270 A: A Novel Inhibitor of Bacterial Protein Synthesis," The Journal of Antibiotics 44 (7):693-701 (1991).

* cited by examiner

*Primary Examiner* — Anish Gupta
*Assistant Examiner* — Jeanette Lieb
(74) *Attorney, Agent, or Firm* — John B. Alexander; Mark W. Milstead

(57) ABSTRACT

This invention relates to a novel antibiotic compounds, pharmaceutically acceptable salts and derivatives thereof, and to methods for obtaining such compounds.

14 Claims, 4 Drawing Sheets

FIG 4

>Bp3714-39
ACGTCATCCCCACCTTCCTCCGAGTTGACCCCGGCAGTCCCCCATGAGTCCCCACCACCCCGAAGG
GCGTGCTGGCAACATGGAGCAAGGGTTGCGCTCGTTGCGGGACTTAACCCAACATCTCACGACACG
AGCTGACGACAGCCATGCACCACCTGTCACCCAGTCCGAAGAGGCGCCTGTCTCCAGGCGTTTCCG
GGTGATGTCAAACCTTGGTAAGGTTCTTCGCGTTGCGTCGAATTAAGCAACATGCTCCGCCGCTTGT
GCGGGCCCCCGTCAATTCCTTTGAGTTTTAGCCTTGCGGCCGTACTCCCCAGGCGGGGCGCTTAAT
GCGTTAGCTCCGGCACGGAGATCGTGGAAGATCCCCACACCTAGCGCCCAACGTTTACAGCGTGGA
CTACCAGGGTATCTAATCCTGTTCGCTCCCCACGCTTTCGCTCCTCAGCGTCAGGTAAGGCCCAGCA
AGCCGCCTTCGCCACCGGTGTTCCTCCTGATATCTGCGCATTTCACCGCTACACCAGGAATTCCACT
TGCCCCTACCTACCTCTAGCCGGCCCGTATCCACCGCAGACCCGCAGTTAAGCTGCGGGCTTTCAC
GGCAGACGCGACCAGCCACCTACGAGCTCTTTACGCCCAATAATTCCGGACAACGCTTGCGCCCTAC
GTATTACCGCGGCTGCTGGCACGTAGTTAGCCGGCGCTTCTTCTGCAGGTACACGTCAACTTCGTCC
CTGCTGAAAGAGGTTTACAACCCGAAGGCCGTCATCCCCCACGCGGCGTCGCTGCGTCAGGCTTCC
GCCCATTGCGCAATATTCCCCACTGCTGCCTCCCGTAGGAGTCTGGGCCGTGTCTCAGTCCCAGTGT
GGCCGGTCGCCCTCTCAGGCCGGCTACCCGTCGTCGCCTTGGTAGGCCACTACCCCACCAACAAGC
TGATAGGCCGCGAGCCCATCCCCAACCGAAAAAACTTTCCACCACCACCCGATGCCGGGGGCGGTC
GTATCCGGTATTAGACCCAGTTTCCCGGGCTTATCCCAGAGTCAGGGGCAGGTTGCTCACGTGTTAC
TCACCCGTTCGCCGCTCGAGTACCCCGAAGGGCCTTTCCGCTCGACTTGCATGTGTTAAGCACGCC
GCCAGCGTTCGTCCTGAGCCAGGATCAAACTCTCCAA

ANTIBACTERIAL COMPOUNDS AND PROCESSES FOR ITS PRODUCTION

This application is a U.S. National Phase filing of International Ser. No. PCT/US2007/025955 filed Dec. 19, 2007, and claims priority to U.S. Application Nos. 60/871,051 filed Dec. 20, 2006, 60/889,591 filed Feb. 13, 2007 and 60/892,988 filed Mar. 5, 2007, the contents of which are incorporated herein by reference in their entirety.

FIELD OF THE INVENTION

This invention relates to novel antibacterial compounds derived from a novel microorganism, *Nonomuraea* sp Bp3714-39, its pharmaceutically acceptable salts and derivatives, and to methods for obtaining and using such compounds.

BACKGROUND OF THE INVENTION

The Streptosporangiaceae family are a subset of a large and complex group of Gram-positive bacteria collectively known as actinomycetes. Over the past few decades these organisms, which are abundant in soil, have generated significant commercial and scientific interest as a result of the large number of therapeutically useful compounds, particularly antibiotics, produced as secondary metabolites. The intensive search for strains able to produce new antibiotics has led to the identification of hundreds of new species.

A representative strain of actinomycetes, belonging to the Pseudonocardiaceae family, *Amycolatopsis* sp. MI481-42F4 produces Amythiamicin A to D, which show antibacterial activity (see *J. Antibiotics,* 47 (1994), 668-674 and 1136-1153, JP1998059997(A), JP1997124503(A), JP1995215989 (A), JP1994263784(A), JP1993310766(A), JP10059997A2 (A), JP09124503A2(A)).

A problem of significant dimension is the increasing incidence of antibiotic resistant bacteria such as the more virulent, methicillin-resistant *Staphylococcus aureus* (MRSA) among clinical isolates found worldwide. As with vancomycin resistant organisms, many MRSA strains are resistant to most of the known antibiotics, but MRSA strains have remained sensitive to vancomycin. However, in view of the increasing reports of vancomycin resistant clinical isolates and growing problem of bacterial resistance, there is an urgent need for new molecular entities effective against the emerging and currently problematic Gram-positive organisms.

This growing multidrug resistance has recently rekindled interest in the search for new structural classes of antibiotics that inhibit or kill these bacteria. New antibiotics have been isolated from fungi and bacteria.

Although many biologically active compounds have been identified from bacteria, there remains the need to obtain novel compounds with enhanced properties. Current methods of obtaining such compounds include screening of natural isolates and chemical modification of existing compounds, both of which are costly and time consuming.

Thus, there exists a considerable need to obtain pharmaceutically active compounds in a cost-effective manner while producing high yield. The present invention solves these problems by providing a novel strain from the Streptosporangiaceae family capable of producing a potent new therapeutic compound and methods to generate such novel compounds

SUMMARY OF THE INVENTION

There remains a need for new treatments and therapies for bacterial infections. There is also a need for compounds useful in the treatment or prevention or amelioration of one or more symptoms of bacterial infections. Furthermore, there is a need for methods for modulating the activity of the elongation factor EF-Tu, using the compounds provided herein.

In one aspect, the invention relates to a compound I of the formula I

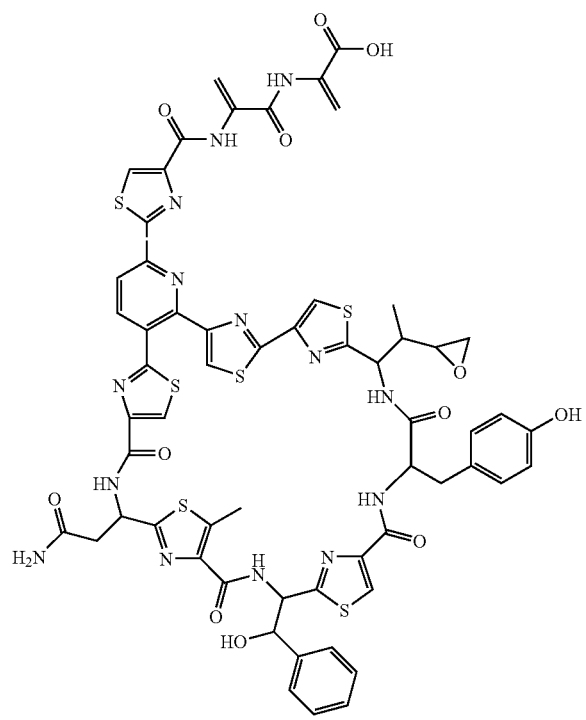

(I)

or a pharmaceutically acceptable salt thereof.

In another aspect, the invention relates to a pharmaceutical composition comprising a compound of the molecular formula $C_{59}H_{50}N_{14}O_{12}S_6$ or a pharmaceutically acceptable salt thereof, together with a pharmaceutically acceptable carrier.

The invention further encompasses a compound having a molecular formula selected from the group consisting of:
$C_{59}H_{52}N_{14}O_{12}S_6$
$C_{59}H_{50}N_{14}O_{12}S_6$
$C_{59}H_{52}N_{14}O_{11}S_6$
$C_{59}H_{52}N_{14}O_{10}S_6$
$C_{59}H_{50}N_{14}O_{13}S_6$
$C_{59}H_{52}N_{14}O_{13}S_6$
$C_{59}H_{51}ClN_{14}O_{12}S_6$
$C_{59}H_{52}N_{14}O_{13}S_6$
$C_{59}H_{50}N_{14}O_{13}S_6$
$C_{59}H_{52}N_{14}O_{12}S_6$
$C_{59}H_{52}N_{14}O_{11}S_6$
$C_{59}H_{50}N_{14}O_{14}S_6$
$C_{59}H_{52}N_{14}O_{14}S_6$
$C_{59}H_{51}ClN_{14}O_{13}S_6$ In another aspect, the invention provides a method of treating a bacterial infection wherein the treatment includes administering to a subject in need thereof a pharmaceutically acceptable amount of a compound of formulas I through XXII.

In another aspect, the invention provides a method of treating an EF-Tu associated-state wherein the treatment includes administering to a subject in need thereof a pharmaceutically acceptable amount of a compound of formulas I through XXII, such that an EF-Tu associated state is treated.

In still another aspect, the invention provides a method of treating, inhibiting or preventing the activity of EF-Tu in a subject in need thereof, which includes administering to the subject a pharmaceutically acceptable amount of a compound of formulas I through XXII. In one aspect, a bacterial infection is treated in a subject in need thereof.

In another aspect, the invention provides a method of treating, inhibiting or preventing the activity of bacteria in a subject in need thereof, which includes administering to the subject a pharmaceutically acceptable amount of a compound of formulas I through XXII wherein the compound interacts with any target in the life cycle of the bacteria. In one embodiment, the target is EF-Tu.

In another aspect, the invention provides a method of treating a bacterial infection in a subject, wherein the treatment includes administering to a subject in need thereof a pharmaceutically acceptable amount of a compound of the formulas I through XXII and a pharmaceutically acceptable carrier, such that the bacterial infection is treated.

In still another aspect, the invention provides a method of treating a bacterial infection wherein the treatment includes administering to a subject in need thereof a pharmaceutically effective amount of at least one compound selected from the group consisting of formulas I through XXII, in combination with a pharmaceutically effective amount of at least one therapeutic agent, such that the bacterial infection is treated. In one aspect, the compound of the invention and the other therapeutic agent are administered as part of the same pharmaceutical composition. In another aspect; at least one compound selected from the group consisting of formulas I through XXII and the other therapeutic agents are administered as separate pharmaceutical compositions, and the compound is administered prior to, at the same time as, or following administration of the other agent.

In another aspect, the invention provides a packaged bacterial infection treatment, comprised of formulas I through XXII, packaged with instructions for using an effective amount of the compound to treat a bacterial infection.

In another aspect, the invention provides a method of treating acne in subject in need thereof, wherein the treatment includes administering to the subject a pharmaceutically acceptable amount of compounds selected from formulas I through XXII.

In another aspect, the invention provides a method of treating bacterial infections such as bacterial endocarditis or bacterial sepsis or both disorders in subject in need thereof, wherein the treatment includes administering to the subject a pharmaceutically acceptable amount of a compound selected from formulas I through XXII.

In yet another aspect, the invention provides a pharmaceutical composition which includes a compound selected from formulas I through XXII and at least one pharmaceutically acceptable carrier or diluent.

The invention further encompasses compounds obtained by a method comprising: a) cultivating Nonomuraea sp Bp3714-39 or an antibiotic producing variant or mutant thereof, wherein the cultivation is performed under aerobic conditions in a nutrient medium comprising at least one source of carbon atoms and at least one source of nitrogen atoms; and b) isolating an antibiotic compound from the bacteria cultivated in step (a).

In one aspect, the antibiotic compound I of the present invention generate a $^{13}C$ NMR spectra essentially as shown in FIG. 1. In another aspect, the antibiotic compound I of the present invention generates an $^{1}H$ NMR spectrum of FIG. 2. In another aspect compound I generates an IR spectrum of FIG. 3.

The invention further encompasses a process for preparing an antibiotic compound; comprising cultivation of Nonomuraea sp Bp3714-39 or an antibiotic producing variant or mutant thereof, in a nutrient medium comprising at least one source of carbon atoms and at least one source of nitrogen atoms, and isolation and purification of the compound. Suitable sources of carbon atoms and nitrogen atoms are exemplified in Table 1 below.

TABLE 1

| Carbon and nitrogen atom sources | |
| --- | --- |
| Carbon atom sources | Nitrogen atom sources |
| Agar | Amino acids mixtures |
| Corn steep liquor | Ammonium |
| Fish oils | Asparagine |
| Fructose | Brain heart infusion |
| Glucose | Casein peptones |
| Glycerol | Corn steep liquor |
| Lactose | Cysteine |
| Malt extract | Meat peptones |
| Mannitol | Nitrate |
| Mannose | Plant peptones |
| Meat extract | Proline |
| Plant oils | Serine |
| Saccharose | Soy flour |
| Skim milk powder | Soy protein |
| Starch | Tyrosine |
| Wheat extract | Valine |
| Yeast extract | Yeast extract |

In another aspect, the cultivation is carried out at a temperature ranging from 18° C. to 40° C. In a further embodiment, the temperature range is 28° C. to 32° C.

In another aspect, the cultivation is carried out at a pH ranging from 6 to 9.

The invention further encompasses the Nonomuraea strain Bp3714-39 having International Depository Authority Accession No. DSM18831.

DETAILED DESCRIPTION OF THE INVENTION

Figure 1:
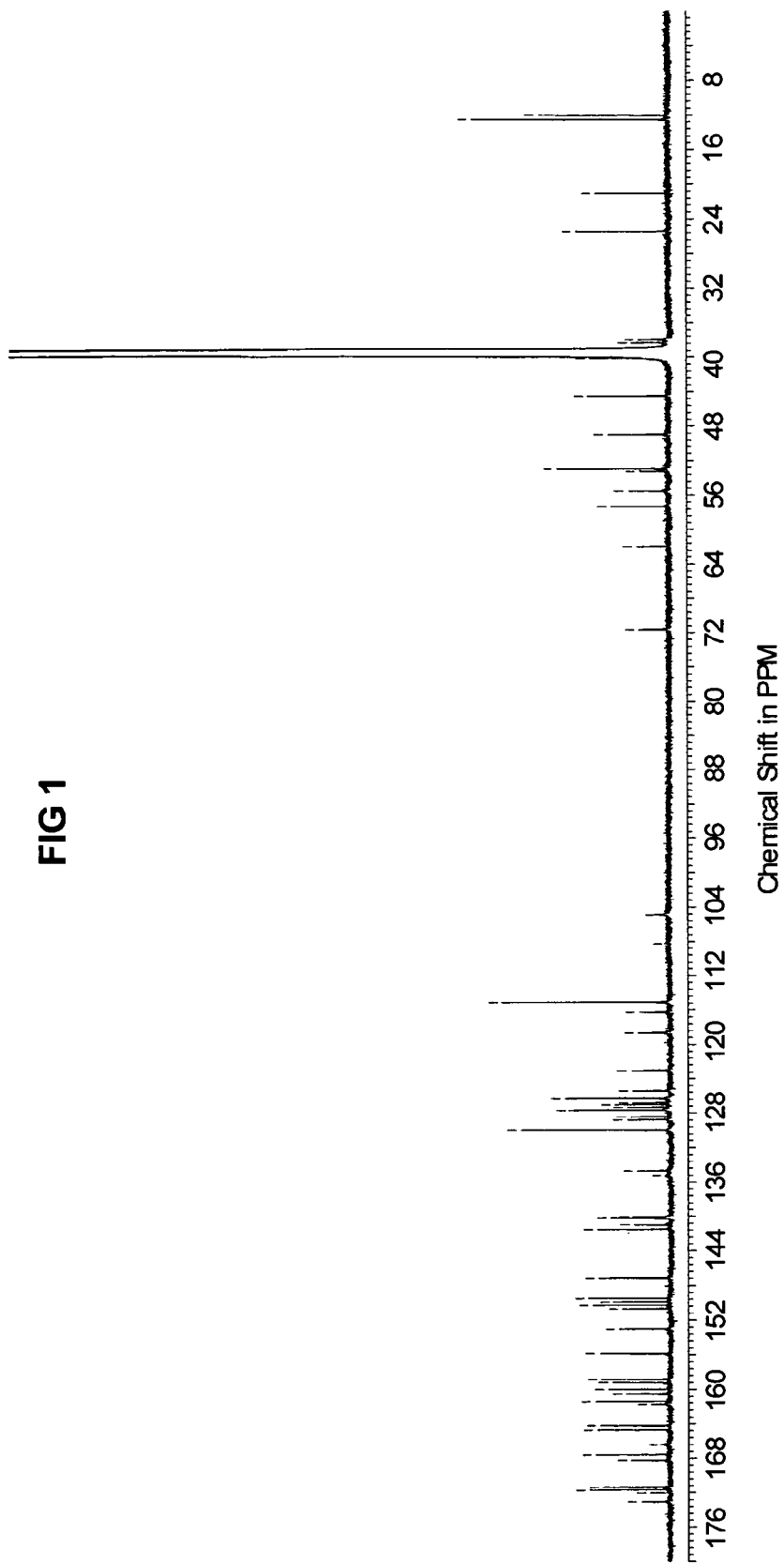
FIG. 1 $^{13}$C-NMR spectrum of compound I in $d_6$-DMSO
FIG. 2 $^{1}$H-NMR spectrum of compound I in $d_6$-DMSO
FIG. 3 IR spectrum (KBr-pellet) of formula I
FIG. 4 16S ribosomal sequence of Nonomuraea sp strain Bp3714-39
Figure 2:
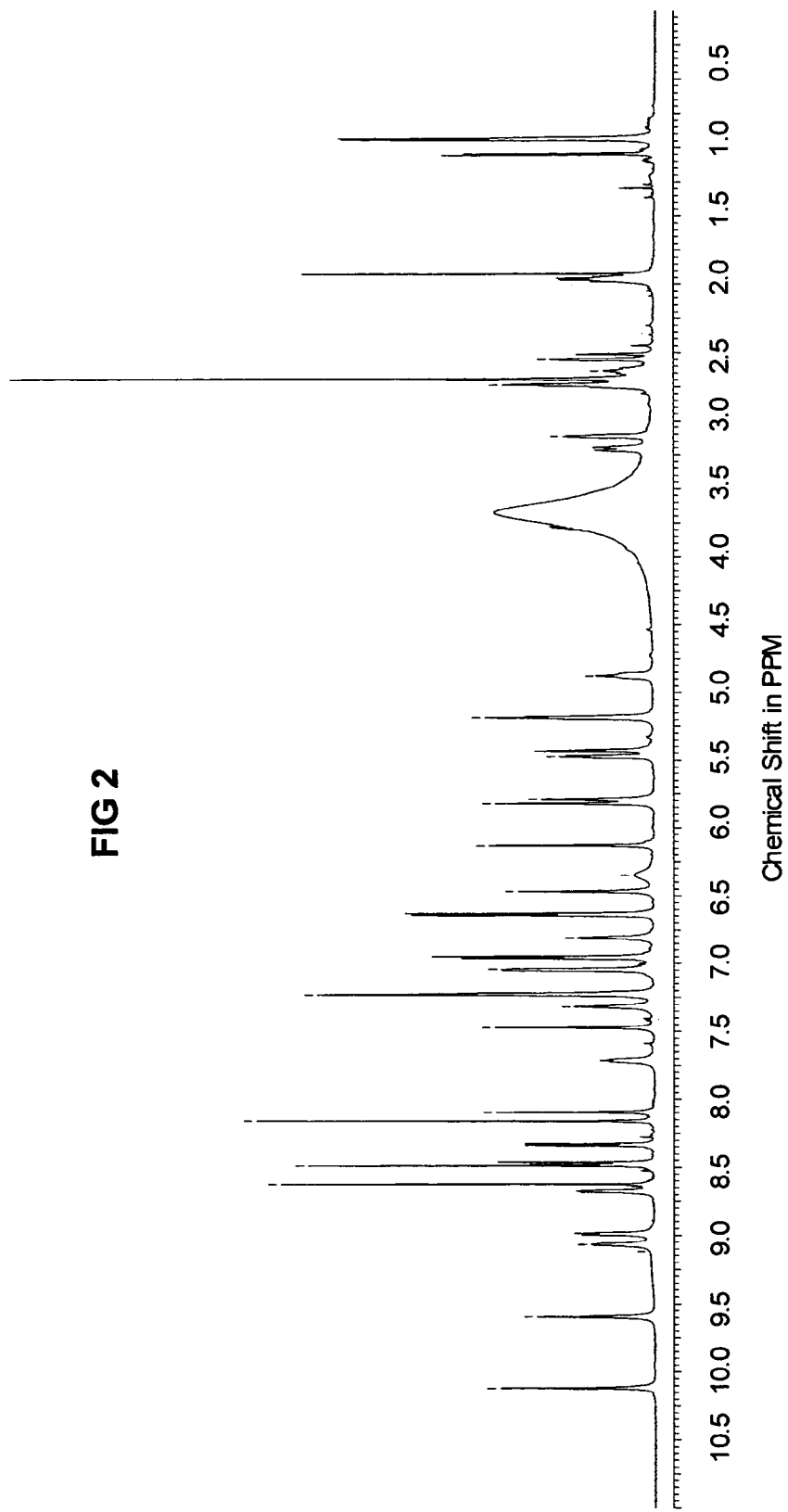
Figure 3:
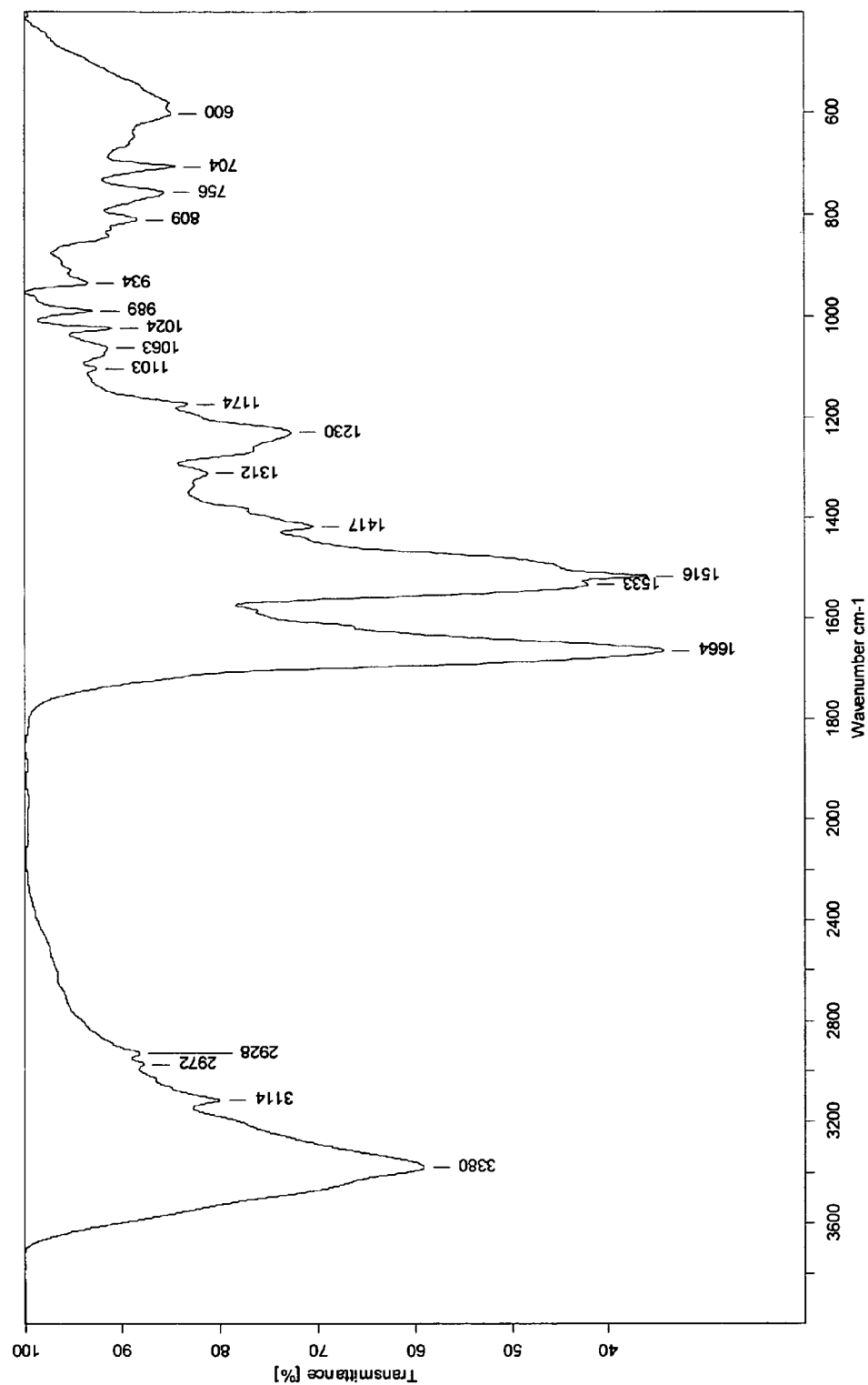

The present invention relates to novel antibiotic compounds, referred to herein as "compound" or "compound of the present invention," which are isolated from a novel strain of actinomycetes, Nonomuraea sp. strain Bp3714-39. This filamentous microorganism was analysed using 16S ribosomal RNA determination and found to belong to the family of Streptosporangiaceae. The 16sRNA sequence is shown in FIG. 4. This organism has been deposited on 2006 Nov. 30, with DSMZ-Deutsche Sammlung Von Mikroorganismen and Zellkulturen GmbH and address Inhoffenstrasse 7B, D-38124 Braunschweig.

The invention is also directed to modulators of the elongation factor EF-Tu. The compounds are particularly useful in interfering with the life cycle of bacteria and in treating or preventing a bacterial infection or physiological conditions associated therewith. The present invention is also directed to methods of combination therapy for inhibiting EF-Tu activity in cells, or for treating or preventing a bacterial infection in subjects using the compounds of the invention or pharmaceutical compositions, or kits thereof.

The invention further relates to pharmaceutically acceptable salts and derivatives of the compounds of the present invention and to methods for obtaining such compounds. One method of obtaining the compound is by cultivating *Nonomuraea* sp. strain Bp3714-39, or a mutant or a variant thereof, under suitable streptomycete conditions, using the fermentation methods described herein.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralization of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallization and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g., using chromatographic methods, distribution methods, (re-) crystallization, and the like.

The following detailed description discloses how to make and use the compounds of the present invention and compositions containing this compound to inhibit bacterial growth and/or specific disease pathways or conditions associated with EF-Tu activity.

Accordingly, certain aspects of the present invention relate to pharmaceutical compositions comprising the compounds of the present invention together with a pharmaceutically acceptable carrier, methods of producing such compounds.

DEFINITIONS

For convenience, the meaning of certain terms and phrases used in the specification, examples, and appended claims, are provided below.

As used herein, the term "compound" refers to a class of macrocyclic compounds. The term includes, but is not limited to, the exemplified compounds of the present invention. The term also encompasses the use of more than one compound of the invention. As used herein, the compounds of the invention also include compounds of this class that can be used as intermediates in chemical syntheses.

The compounds of the present invention have valuable pharmacological properties and are useful in the treatment of diseases. In certain embodiments, compounds of the invention are useful in the treatment of bacterial infections.

The term "use" includes any one or more of the following embodiments of the invention, respectively: the use in the treatment of bacterial infections; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. The term "use" further includes embodiments of compositions herein which bind to a compound of the present invention sufficiently to serve as tracers or labels, so that when coupled to a flour or tag, or made radioactive, can be used as a research reagent or as a diagnostic or an imaging agent.

In certain embodiments, the compound of the present invention is used for treating EF-Tu-associated diseases or conditions, and use of the compound as an inhibitor of any one or more EF-Tu molecules, including nucleic acid sequences or proteins comprising EF-Tu. It is envisioned that a use can be a treatment of inhibiting one or more isoforms of EF-Tu.

As used herein, the term "bacterial infection(s)" includes, but is not limited to, bacterial infections that occur in mammals, fish and birds as well as disorders related to bacterial infections that may be treated or prevented by administering antibiotics such as the compounds of the present invention. In addition to treating infections caused by multi-drug resistant strains of *Staphyloccocus aureus, Streptococcus pneumoniae, Mycobacterium tuberculosis* and *Enterococci*, the compounds of the present invention are useful in treating infections caused by other bacteria including, but not limited to, *Clostridium difficile, Propionibacterium acnes, Bacteroides fagiles, Neisseria gonorrhoeae, Branhamella catarrhalis, Haemophilus influenzae, E. coli, Pseudomonas aeruginosa, Proteus vulgaris, Klebsiella pneumonia,* and *Chlamydia trachomatis*.

Bacterial infections and disorders related to such infections include, but are not limited to, the following: acne, rosacea, skin infection, pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Peptostreptococcus* spp. or *Pseudomonas* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C-F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; sexually transmitted diseases related to infection by *Chlamydia trachomatis*, *Haemophilus ducreyi*, *Treponema pallidum*, *Ureaplasma urealyticum*, or *Nesseria gonorrheae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp., odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium acne*; atherosclerosis related to infection by *Helicobacter pylori* or *Chlamydia pneumoniae*; or the like.

Further bacterial infections and disorders related to such infections that may be treated or prevented in animals include, but are not limited to, the following: bovine respiratory disease related to infection by *P. haemolytica., P. multocida, Mycoplasma bovis*, or *Bordetella* spp.; cow enteric disease related to infection by *E. coli* or protozoa (i.e., *coccidia, cryptosporidia*, etc.), dairy cow mastitis related to infection by *S. aureus, S. uberis, S. agalactiae, S. dysgalactiae, Klebsiella* spp., *Corynebacterium*, or *Enterococcus* spp.; swine respiratory disease related to infection by *A. pleuropneumoniae, P. multocida*, or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*, cow premature abortion related to infection by protozoa (i.e., neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; dental or mouth infections in dogs and goats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., *Trichomonas* spp. or *Prevotella* spp. Other bacterial infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Further bacterial infections and disorders related to such infections that may be treated or prevented in animals include, but are not limited to, dermatological disorders, such as acne, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, antibacterial prophylaxis in immunosuppressed patients, such as patients receiving cancer chemotherapy, or organ transplant patients and chronic diseases caused by infectious organisms, e.g., arteriosclerosis.

The compounds of the present invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

The compounds of the present invention can possess one or more asymmetric carbon atoms and can exist as optical isomers forming mixtures of racemic or non-racemic compounds. The compounds of the present invention are useful as single isomers or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes.

The terms "antibiotic producing microorganism" and "producer of antibiotic compounds," as used herein, refer to a microorganism that carries genetic information necessary to produce the antibiotic compounds of the present invention and/or derivatives thereof, whether or not the organism naturally produces the compound. The terms apply equally to organisms in which the genetic information to produce the antibiotic compound is found in the organism as it exists in its natural environment, and to organisms in which the genetic information is introduced by recombinant techniques.

Specific organisms contemplated herein include, without limitation, organisms of the actinomycete suborder Streptosporanqineae including the families Nocardiopsaceae, Streptosporanqiaceae and Thermomonosporaceae, of which preferred genera include *Acrocarpospora, Actinomadura, Herbidospora, Microbispora, Microtetraspora, Nocardiopsis, Nonomuraea* ((*Nonomuria* sic, corrected by Chiba et al (1999) to *Nonomuraea*) a reclassified genus as reported by Zhenshui Zhang, Yue Wang and Jisheng Ruan in the International Journal of Systematic Bacteriology (1998), 48, 411-422)), *Planobispora, Planomonospora, Planopolyspora, Planotetraspora* or *Streptosporangium* The terms are intended to encompass all organisms containing genetic information necessary to produce an antibiotic compound. A preferred producer of an antibiotic compound includes *Nonomuraea* microbial strain Bp3714-39; a deposit of which was made on 2006 Nov. 30, under Accession No. DSM 18831.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

The term "pharmaceutically acceptable salt" refers to both acid addition salts and base addition salts. The nature of the salt is not critical, provided that it is pharmaceutically acceptable. Exemplary acid addition salts include, without limitation, hydrochloric, hydrobromic, hydroiodic, nitric, carbonic, sulphuric, phosphoric, formic, acetic, citric, tartaric, succinic, oxalic, malic, glutamic, propionic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, beta-hydroxybutyric, malonic, galactaric, galacturonic acid and the like. Suitable pharmaceutically acceptable base addition salts include, without limitation, metallic salts made from aluminium, calcium, lithium, magnesium, potassium, sodium and zinc or organic salts made from N,N'-dibenzylethylenediamine, chloroprocaine, choline, diethanolamine, ethylenediamine, N-methylglucamine, lysine, procaine and the like. Additional examples of pharmaceutically acceptable salts are listed in Journal of Pharmaceutical Sciences (1977) 66:2. All of these salts may be prepared by conventional means from an antibiotic compound by treating the compound with the appropriate acid or base.

II Antibiotic Compounds

In certain aspects, the compound of the present invention is characterized as a modulator of EF-Tu, including a prokaryotic EF-Tu, and especially including a bacterial EF-Tu. In a preferred embodiment, the compound of the invention is an EF-Tu inhibitor.

EF-Tu is one of the most abundant proteins in bacteria, as well as one of the most highly conserved, and in a number of species the gene is duplicated with identical function. Bacterial protein synthesis requires EF-Tu chaperone proteins. When bound to GTP, EF-Tu can form a complex with most aminoacylated tRNAs, loading the tRNA onto the ribosome. Consequently, bacterial infection has been associated with the activity of EF-Tu. Without being bound by theory, it is believed that the disruption of EF-Tu synthesis or activity in the life cycle of a bacteria may prevent or inhibit bacterial function and/or proliferation. The compounds of the present invention are particularly useful in interfering with transcription or protein translation of Gram-positive and/or Gram-negative bacteria.

As used herein, the term "EF-Tu-associated state" or "EF-Tu-associated disorder" include disorders and states (e.g., a disease state) that are associated with the activity of EF-Tu. A non-limiting example of an EF-Tu associated disorder is a bacterial infection in a subject.

The present invention includes treatment of bacterial infections, as well as EF-Tu-associated disorders, as described above, but the invention is not intended to be limited to the manner by which the compound performs its intended function of treatment of a disease. The present invention includes treatment of diseases described herein in any manner that allows treatment to occur, e.g., bacterial infection.

In certain aspects, the invention provides a pharmaceutical composition of any of the compounds of the present invention. In a related aspect, the invention provides a pharmaceutical composition of any of the compounds of the present invention and a pharmaceutically acceptable carrier or excipient of any of these compounds. In certain aspects, the invention includes the compounds as novel chemical entities.

In one aspect, the invention includes a packaged bacterial infection treatment. The packaged treatment includes a compound of the invention packaged with instructions for using an effective amount of the compound of the invention for an intended use.

The compounds of the present invention are suitable as active agents in pharmaceutical compositions that are efficacious particularly for treating bacterial infections. The pharmaceutical composition in various embodiments has a pharmaceutically effective amount of the present active agent along with other pharmaceutically acceptable excipients, carriers, fillers, diluents and the like. The phrase, "pharmaceutically effective amount" as used herein indicates an amount necessary to administer to a host, or to a cell, issue, or organ of a host, to achieve a therapeutic result, especially an antibacterial infection effect, e.g., inhibition of proliferation of a bacterium, or of any other bacterial infection.

In other aspects, the present invention provides a method for inhibiting the activity of an EF-Tu protein. The method includes contacting a cell with any of the compounds of the present invention. In a related aspect, the method further provides that the compound is present in an amount effective to selectively inhibit the activity of an EF-Tu protein.

In other aspects, the present invention provides a use of any of the compounds of the invention for manufacture of a medicament to treat a bacterial infection in a subject.

In other aspects, the invention provides a method of manufacture of a medicament, including formulating any of the compounds of the present invention for treatment of a subject.

The term "treat," "treated," "treating" or "treatment" includes the diminishment or alleviation of at least one symptom associated or caused by the state, disorder or disease being treated. In certain aspects, the treatment comprises the induction of a bacterial infection, followed by the activation of the compound of the invention, which would in turn diminish or alleviate at least one symptom associated or caused by the bacterial infection being treated. For example, treatment can be diminishment of one or several symptoms of a disorder or complete eradication of a disorder.

The term "subject" is intended to include organisms, e.g., prokaryotes and eukaryotes, which are capable of suffering from or afflicted with a bacterial infection. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a bacterial infection, and for diseases or conditions described herein. In another embodiment, the subject is a cell.

The language "EF-Tu-modulating compound," "modulator of EF-Tu" or "EF-Tu inhibitor" refers to compounds that modulate, e.g., inhibit, or otherwise alter, the activity of EF-Tu. Examples of EF-Tu-modulating compounds include compounds of formulas I through XXII (including pharmaceutically acceptable salts thereof, as well as enantiomers, stereoisomers, rotamers, tautomers, diastereomers, or racemates thereof).

Additionally, a method of the invention includes administering to a subject an effective amount of an EF-Tu-modulating compound of the invention, e.g., EF-Tu-modulating compounds of formulas I through XXII (including pharmaceutically acceptable salts thereof, as well as enantiomers, stereoisomers, rotamers, tautomers, diastereomers, or racemates thereof).

The EF-Tu modulating compounds of the invention and pharmaceutically acceptable salts thereof, can be formulated for oral, intravenous, intramuscular, subcutaneous, topical or parenteral administration for the therapeutic or prophylactic treatment of diseases, particularly bacterial infections and disorders described herein. For oral or parental administration, compounds of the present invention can be mixed with conventional pharmaceutical carriers and excipients and used in the form of tablets, capsules, elixirs, suspensions, syrups, wafers and the like. The compositions comprising a compound of this present invention will contain from about 0.1% to about 99.9%, about 1% to about 98%, about 5% to about 95%, about 10% to about 80% or about 15% to about 60% by weight of the active compound.

The pharmaceutical preparations disclosed herein are prepared in accordance with standard procedures and are administered at dosages that are selected to reduce, prevent, or eliminate bacterial infections. (See, e.g., Remington's Pharmaceutical Sciences, Mack Publishing Company, Easton, Pa.; and Goodman and Gilman, Pharmaceutical Basis of Therapeutics, Pergamon Press, New York, N.Y., the contents of which are incorporated herein by reference, for a general description of the methods for administering various antimicrobial agents for human therapy). The compositions of the present invention can be delivered using controlled (e.g., capsules) or sustained release delivery systems (e.g., bioerodable matrices). Exemplary delayed release delivery systems for drug delivery that are suitable for administration of the compositions of the invention (preferably of formulas I-XI) are described in U.S. Pat. No. 4,452,775 (issued to Kent), U.S. Pat. No. 5,239,660 (issued to Leonard), U.S. Pat. No. 3,854,480 (issued to Zaffaroni).

The pharmaceutically acceptable compositions of the present invention comprise one or more compounds of the present invention in association with one or more non-toxic, pharmaceutically acceptable carriers and/or diluents and/or adjuvants and/or excipients, collectively referred to herein as "carrier" materials, and if desired other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain crosarmellose sodium, microcrystalline cellulose, sodium starch glycolate and alginic acid.

Tablet binders that can be included are acacia, methylcellulose, sodium carboxymethylcellulose, polyvinylpyrrolidone (Providone), hydroxypropyl methylcellulose, sucrose, starch and ethylcellulose.

Lubricants that can be used include magnesium stearate or other metallic stearates, stearic acid, silicon fluid, talc, waxes, oils and colloidal silica.

Flavouring agents such as peppermint, oil of wintergreen, cherry flavouring or the like can also be used. It may also be desirable to add a coloring agent to make the dosage form more aesthetic in appearance or to help identify the product comprising a compound of the present invention.

For oral use, solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica or talc: disintegrants, for example, potato starch, flavoring or coloring agents, or acceptable wetting agents. Oral liquid preparations generally are in the form of aqueous or oily solutions, suspensions, emulsions, syrups or elixirs and may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl parahydroxybenzoate, propylene glycol, sorbitol, or sorbic acid.

For intravenous (iv) use, compounds of the present invention can be dissolved or suspended in any of the commonly used intravenous fluids and administered by infusion. Intravenous fluids include, without limitation, physiological saline or Ringer's solution.

Formulations for parental administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium-chloride, and/or various buffers.

For intramuscular preparations, a sterile formulation of compounds of the present invention or suitable soluble salts forming the compound, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For topical use the compounds of present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compound of the present invention can be in powder form for reconstitution in the appropriate pharmaceutically acceptable carrier at the time of delivery. In another embodiment, the unit dosage form of the compound can be a solution of the compound or a salt thereof in a suitable diluent in sterile, hermetically sealed ampoules.

The amount of the compound of the present invention in a unit dosage comprises a therapeutically-effective amount of at least one active compound of the present invention which may vary depending on the recipient subject, route and frequency of administration. A recipient subject refers to a plant, a cell culture or an animal such as an ovine or a mammal including a human.

According to this aspect of the present invention, the novel compositions disclosed herein are placed in a pharmaceutically acceptable carrier and are delivered to a recipient subject (including a human subject) in accordance with known methods of drug delivery. In general, the methods of the invention for delivering the compositions of the invention in vivo utilize art-recognized protocols for delivering the agent with the only substantial procedural modification being the substitution of the compounds of the present invention for the drugs in the art-recognized protocols.

Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the present invention for the agents used in the art-recognized protocols.

The compounds of the present invention provide a method for treating bacterial infections. As used herein, the term "unit dosage" refers to a quantity of a therapeutically effective amount of a compound of the present invention that elicits a desired therapeutic response. As used herein, the phrase "therapeutically effective amount" means an amount of a compound of the present invention that prevents the onset, alleviates the symptoms, or stops the progression of a bacterial infection. The term "treating" is defined as administering, to a subject, a therapeutically effective amount of at least one compound of the present invention, both to prevent the occurrence of a bacterial infection or to control or eliminate a bacterial infection, inflammation or pre-cancerous or cancer condition. The term "desired therapeutic response" refers to treating a recipient subject with a compound of the present invention such that a bacterial or inflammatory condition or pre-cancer or cancer condition is reversed, arrested or prevented in a recipient subject.

The compounds of the present invention can be administered as a single daily dose or in multiple doses per day. The treatment regime may require administration over extended periods of time, e.g., for several days or for from two to four weeks. The amount per administered dose or the total amount administered will depend on such factors as the nature and severity of the disease condition, the age and general health of the recipient subject, the tolerance of the recipient subject to the compound and the type of the bacterial infection or disorder related to bacterial infections.

A compound according to this invention may also be administered in the diet or feed of a patient or animal. The diet for animals can be normal foodstuffs to which the compound can be added or it can be added to a premix.

The compounds of the present invention may be taken in combination, together or separately with any known clinically approved antibiotic, inflammation or anti-cancer agent to treat a recipient subject in need of such treatment.

In another aspect, the invention relates to antibiotic compounds having, the chemical structure represented by the following formula I:

(I)

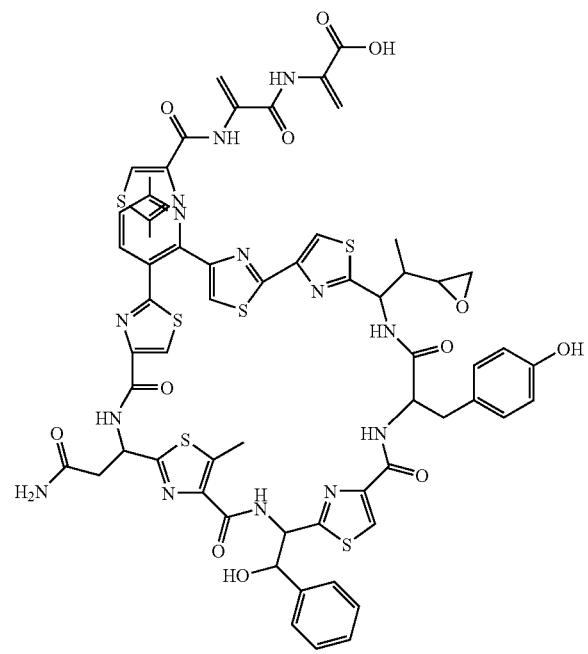

The compounds of the invention may be characterized by any one or more of its physicochemical and spectral properties given below, such as its mass, UV, IR and NMR spectroscopic data.

Exemplary compounds of the present invention (e.g., formulas I through XI) are represented as follows:

(I)

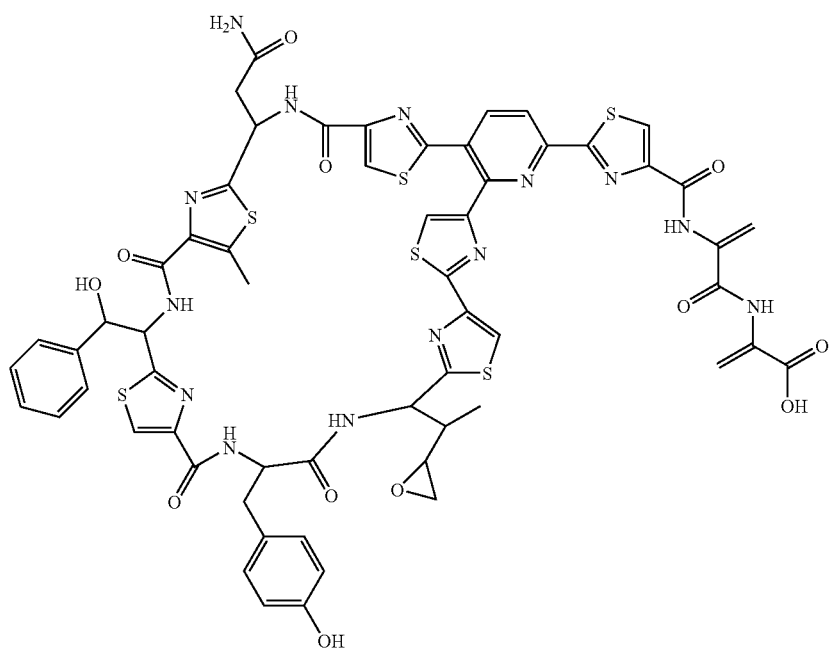

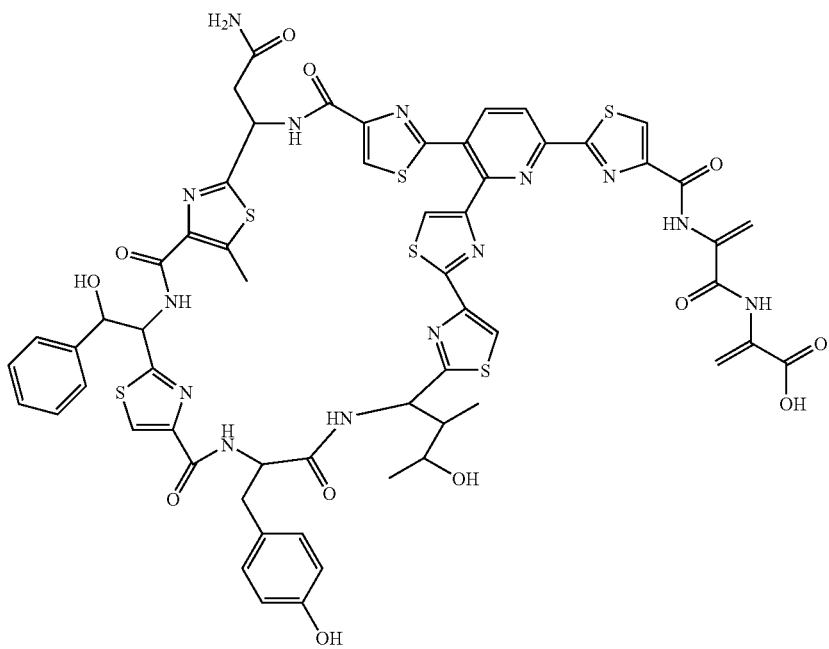
(II)
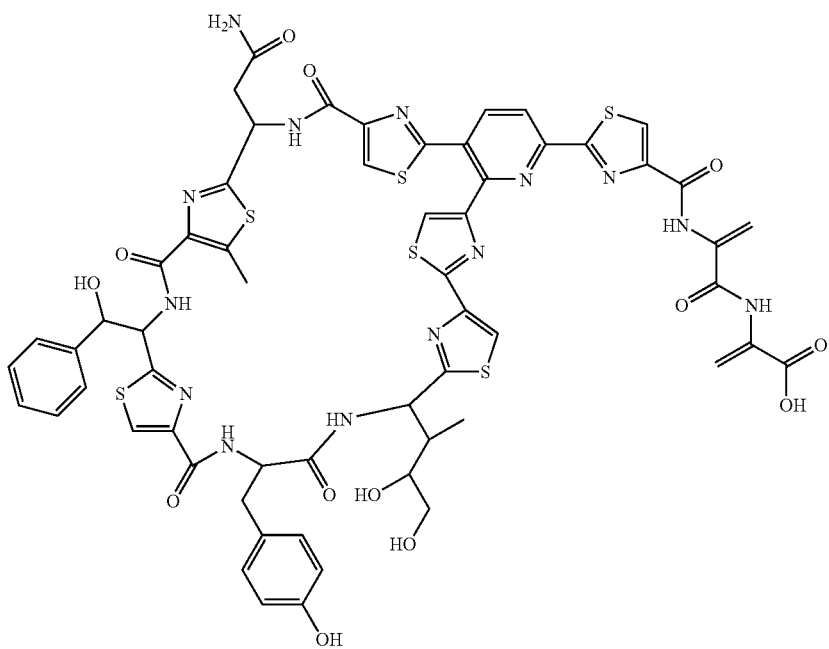
(III)

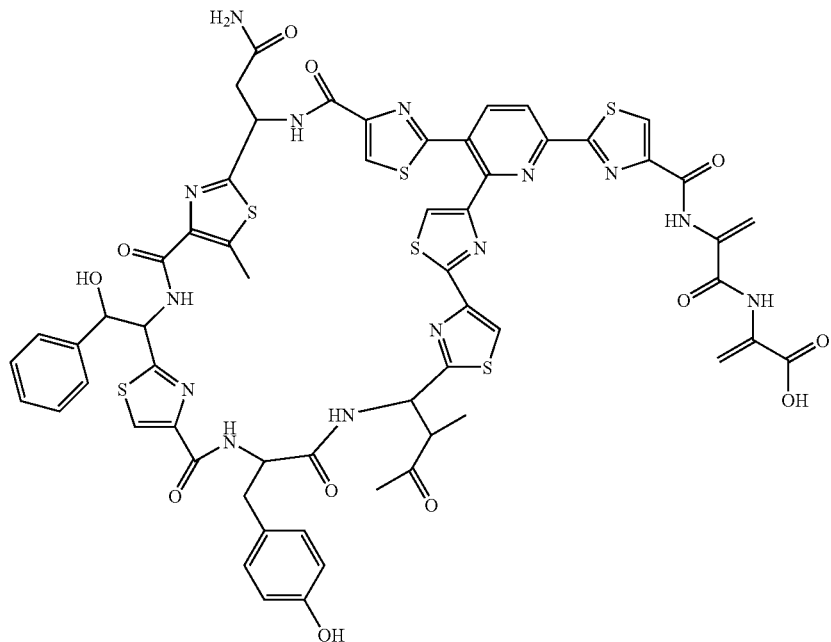
(IV)
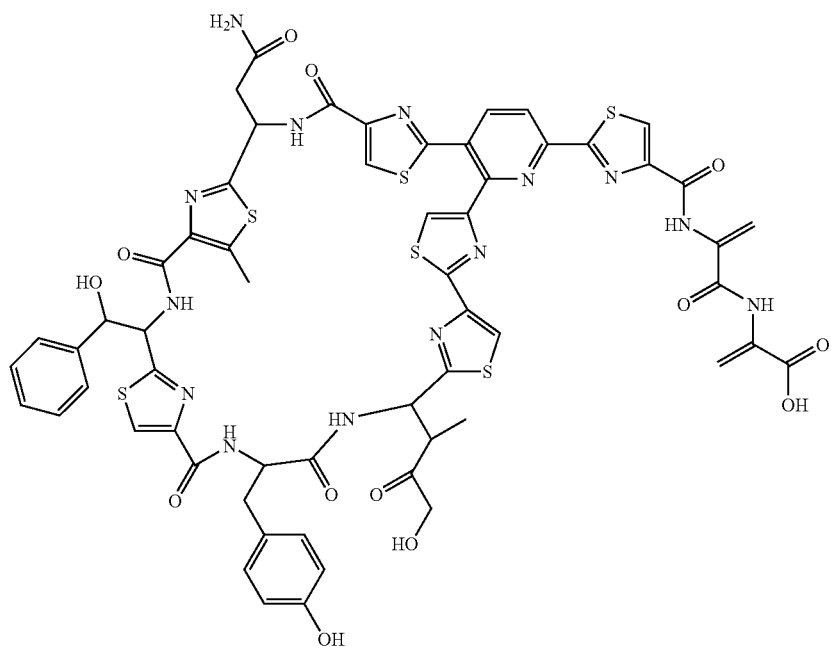
(V)

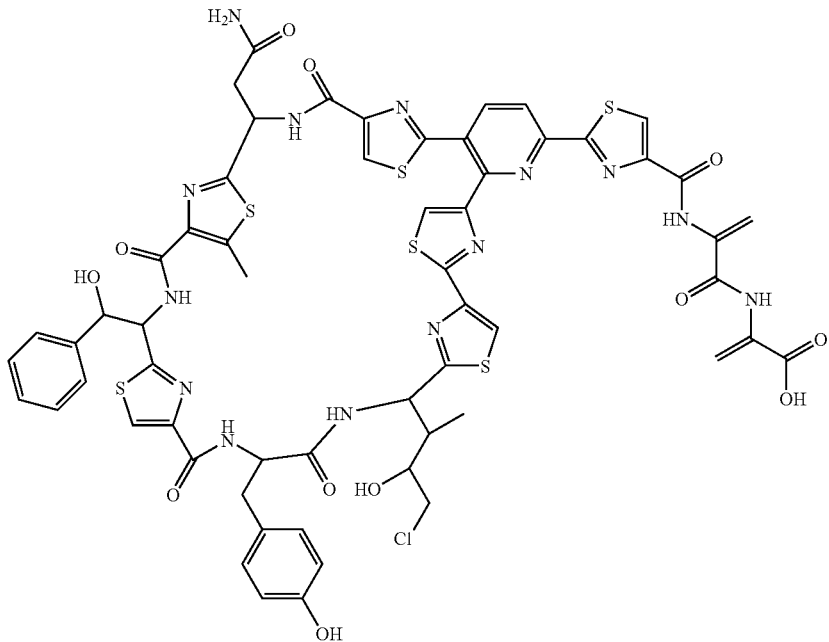
(VI)
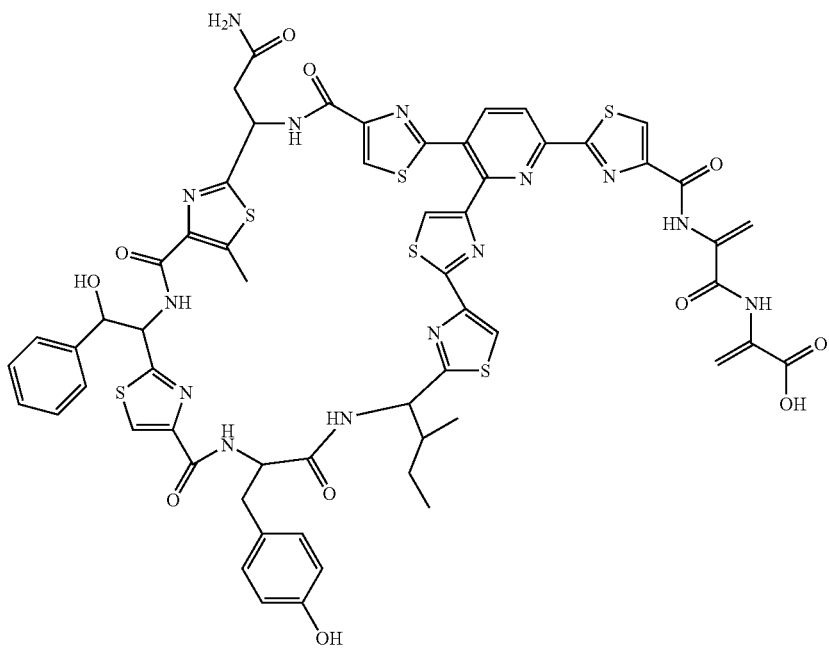
(VII)

(VIII)
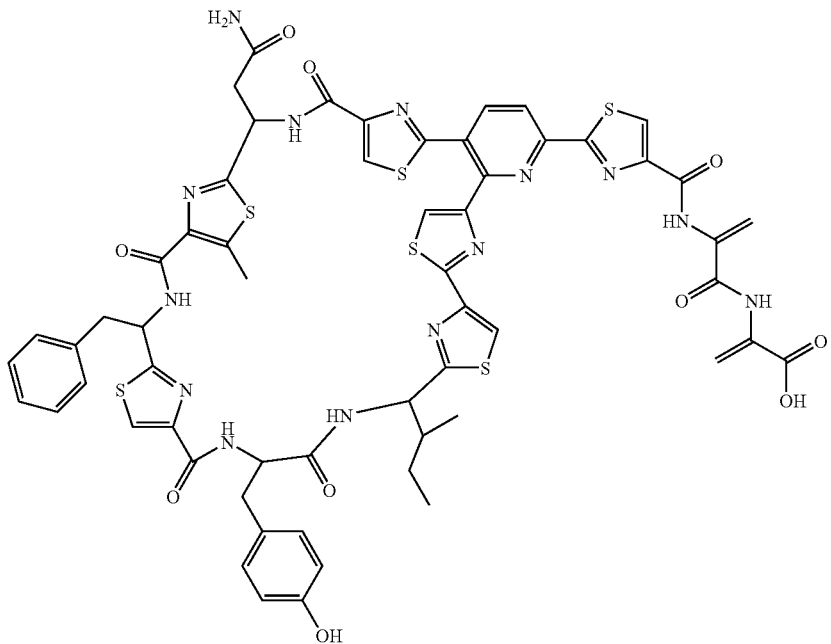
(IX)
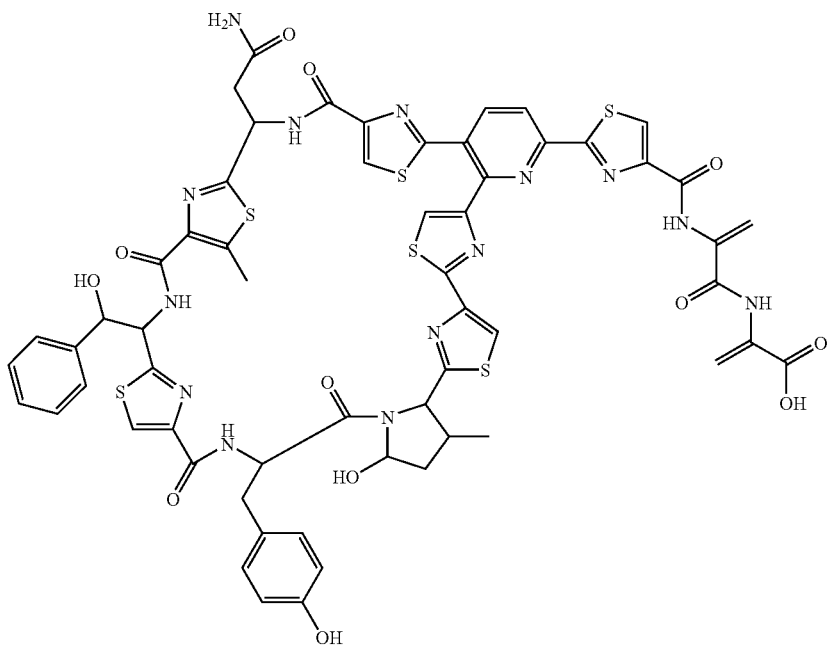

-continued
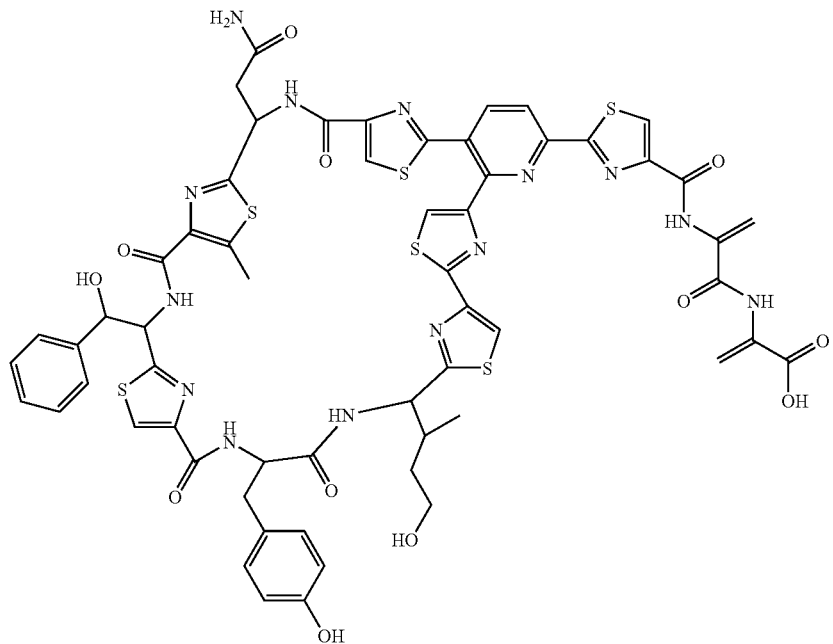
(X)
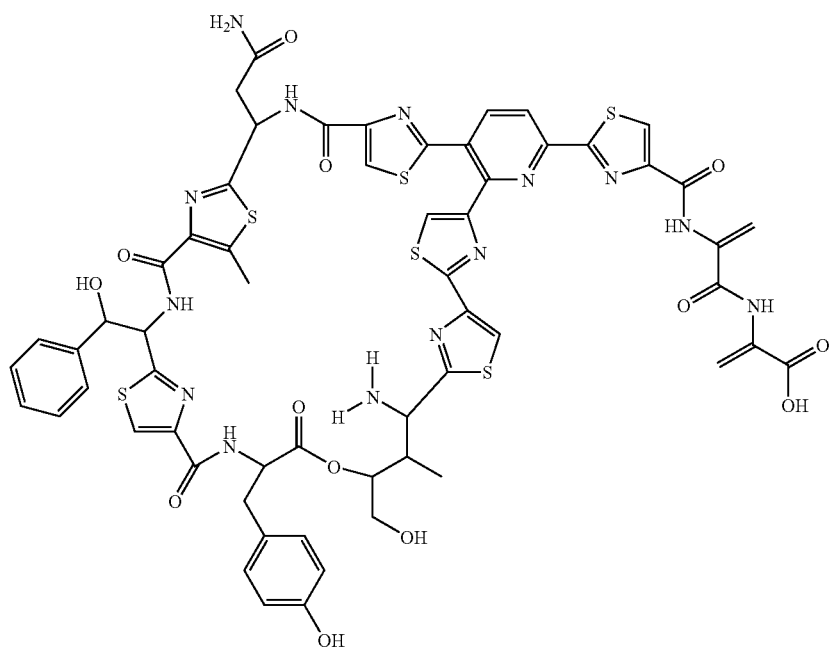
(XI)

including pharmaceutically acceptable salts thereof, as well as enantiomers, stereoisomers, rotamers, tautomers, diastereomeres, atropisomers or racemates thereof. The compounds of the invention are also referred to herein as "antibiotitics" and "EF-Tu inhibitors"

Other exemplary compounds of the present invention (e.g., formulas XII through XXII) are represented as follows:

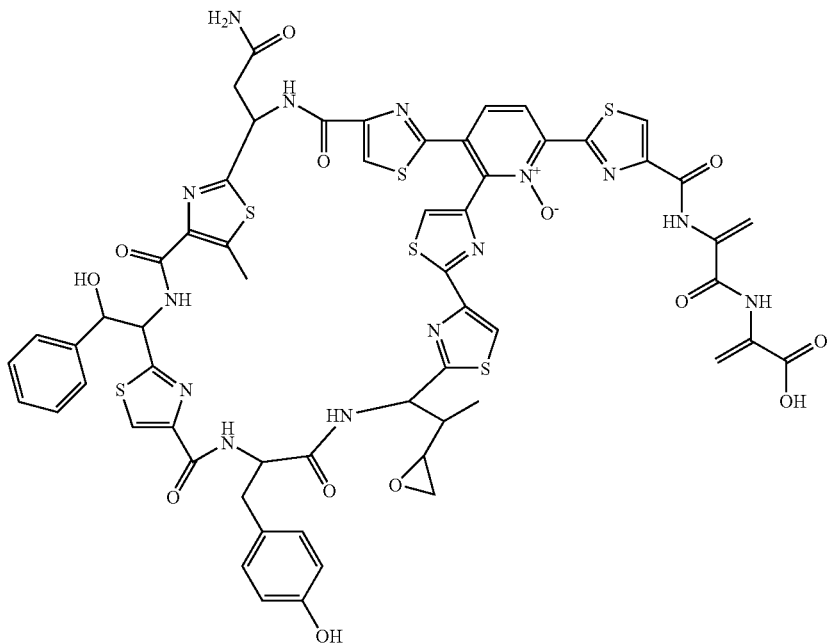

(XII)

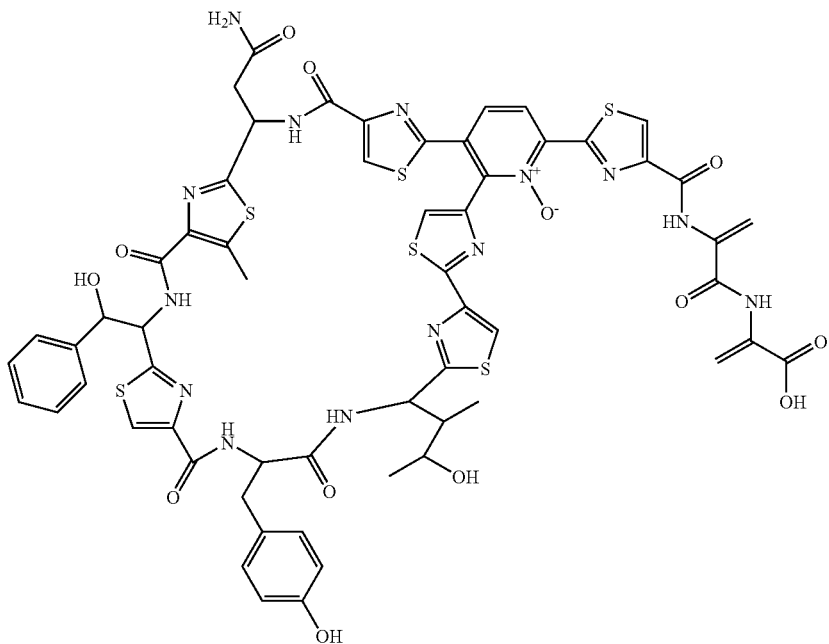

(XIII)

-continued
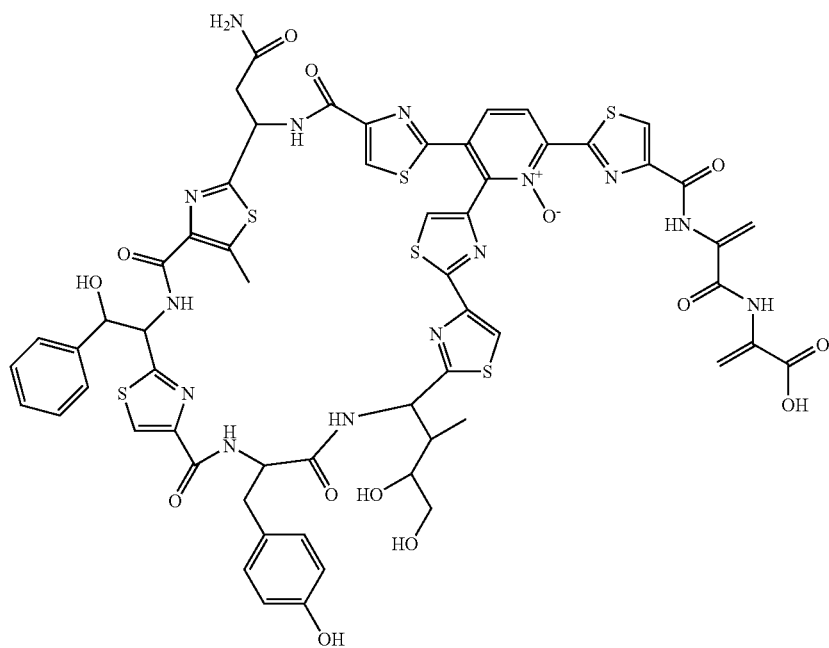
(XIV)
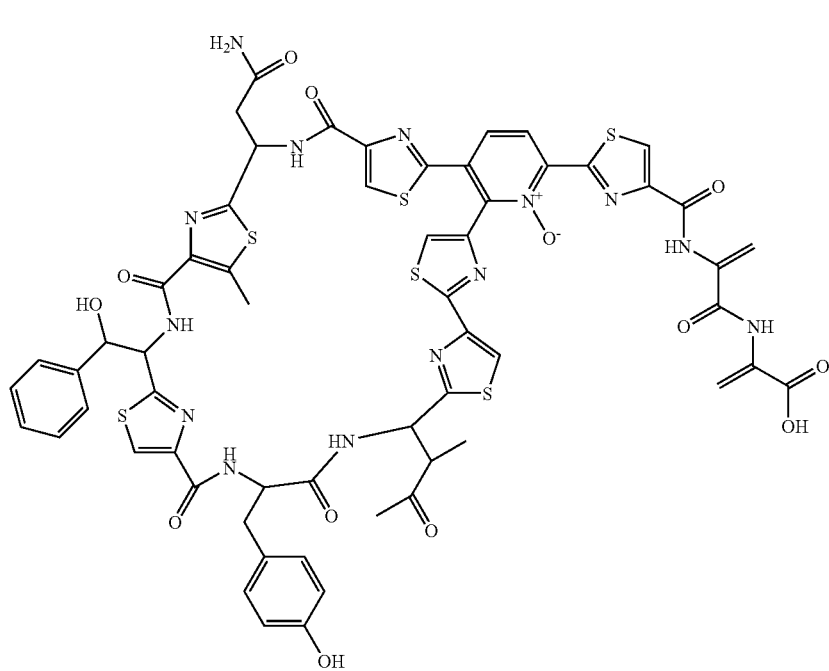
(XV)

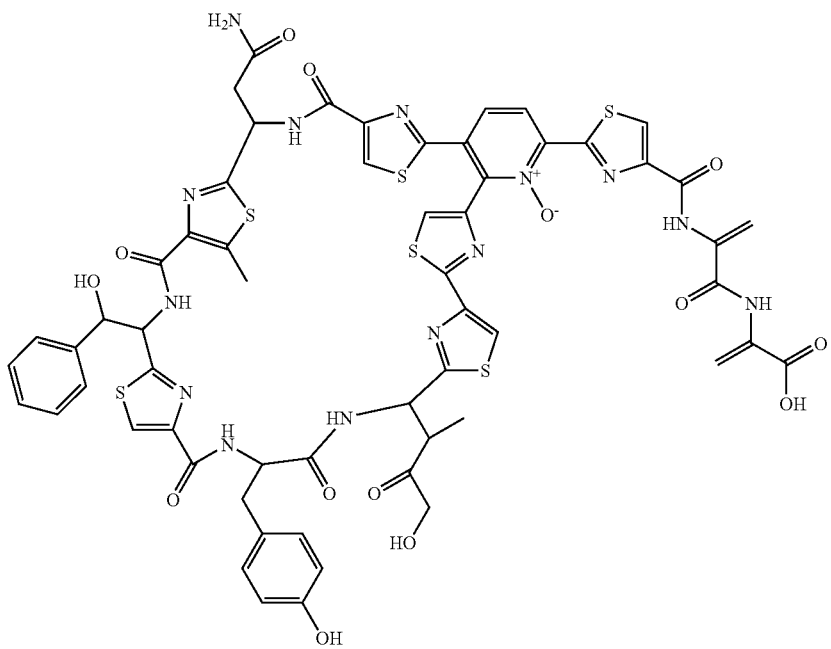
(XVI)
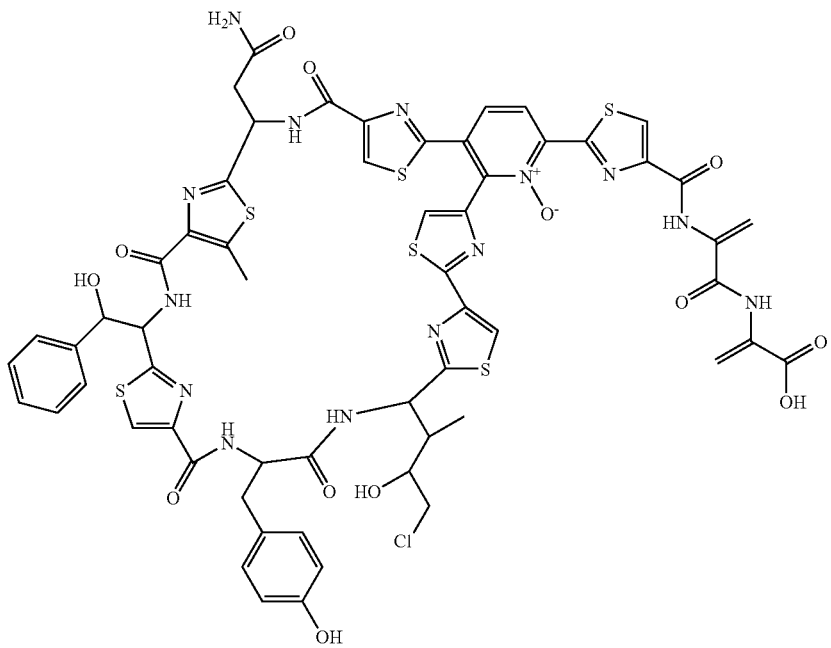
(XVII)

-continued
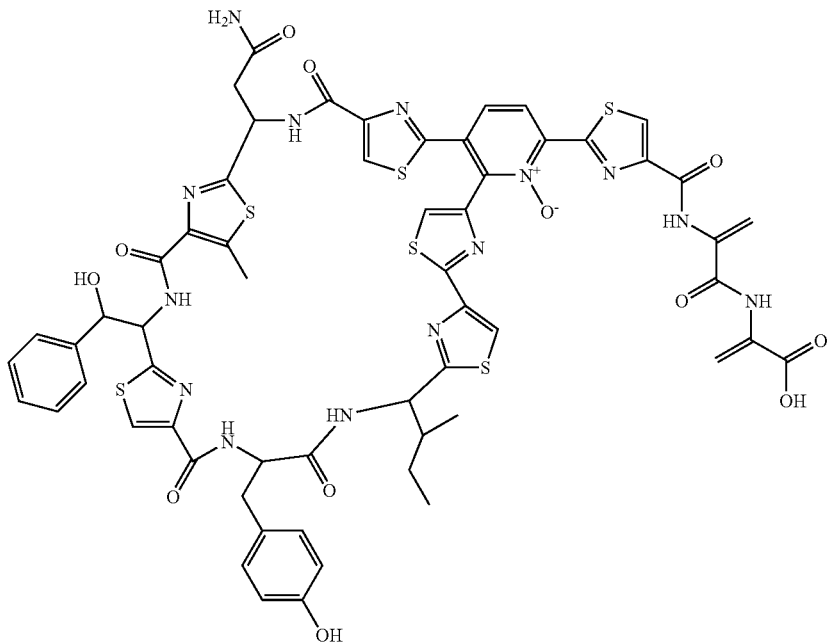
(XVIII)
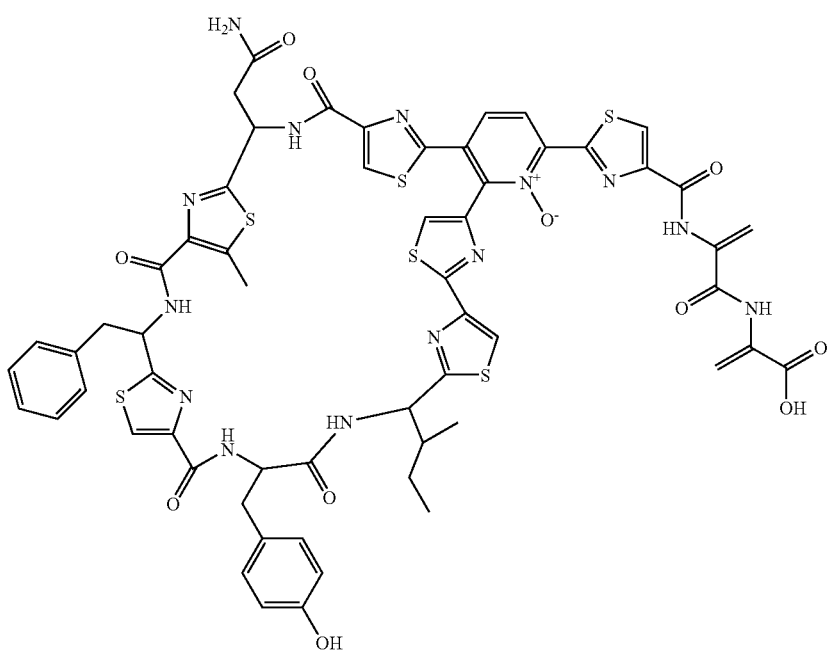
(XIX)

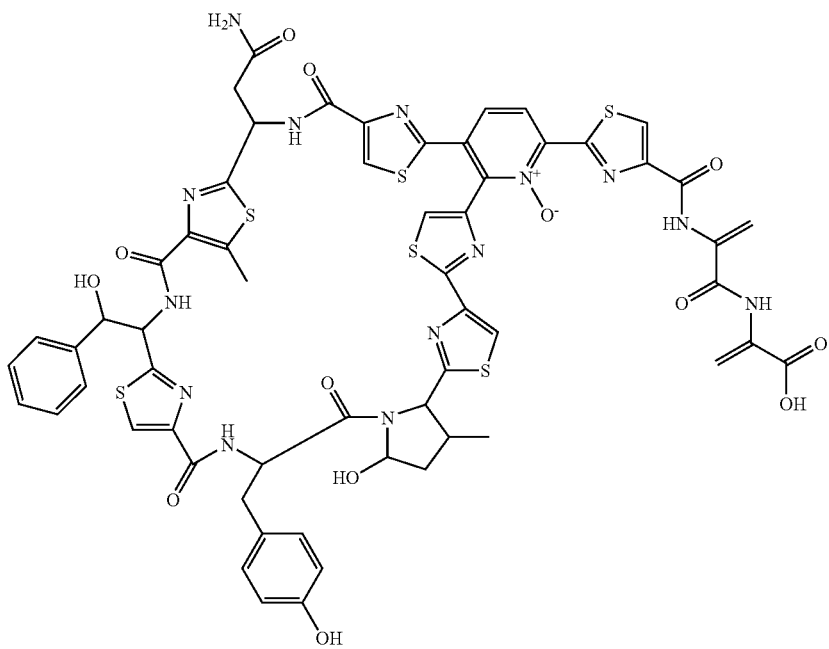
(XX)
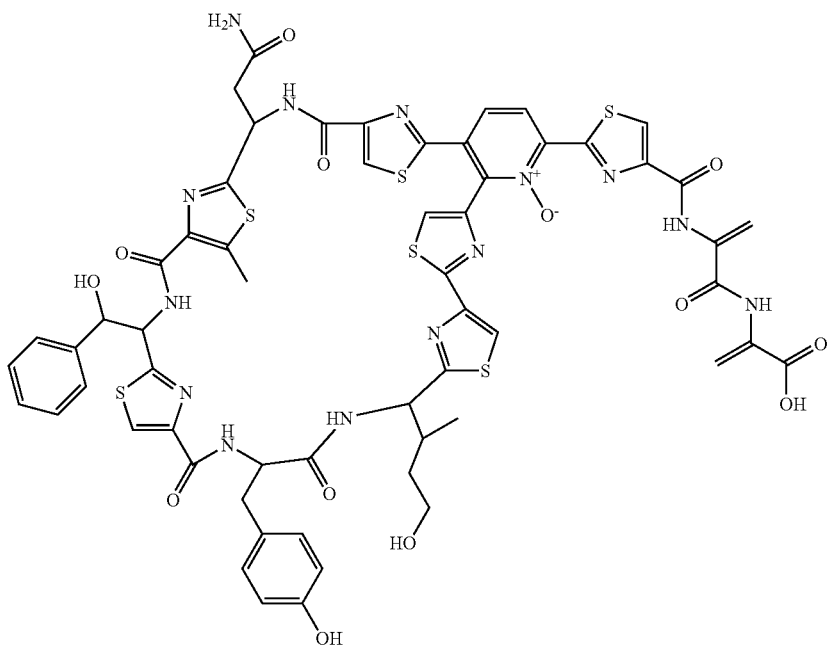
(XXI)

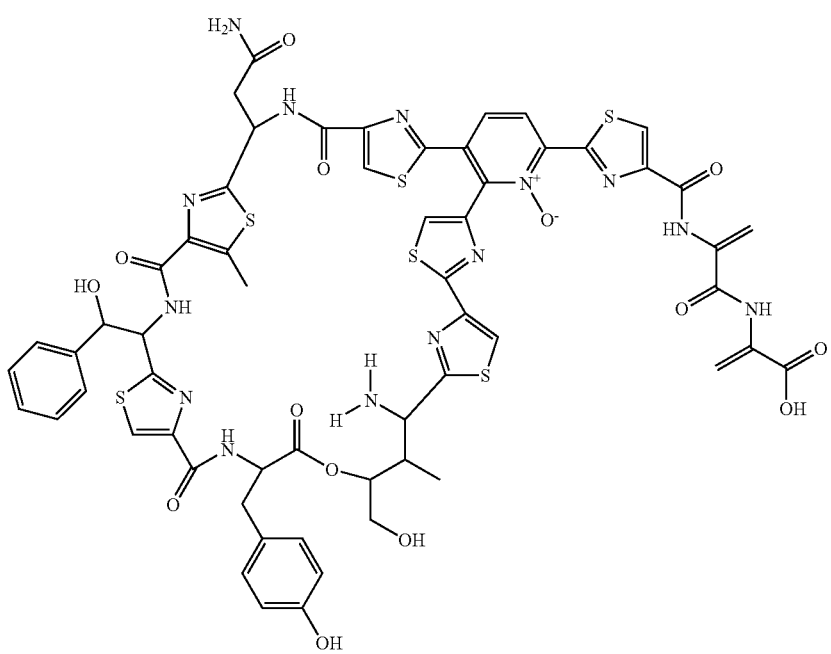

(XXII)

including pharmaceutically acceptable salts thereof, as well as enantiomers, stereoisomers, rotamers, tautomers, diastereomeres, atropisomers or racemates thereof.

The compounds of this invention may be formulated into pharmaceutical compositions comprised of compounds of the present invention in combination with a pharmaceutical acceptable carrier, as discussed herein.

III. Method of Making Antibiotic Compounds by Fermentation

In one aspect, compounds I-XI are obtained by cultivating a novel strain of *Nonomuraea*, namely *Nonomuraea* sp. strain Bp3714-39. Strain Bp3714-39 was deposited on 30 Nov. 2006 with the DSMZ. The deposit of the strain was made under the terms of the Budapest Treaty on the International Recognition of the Deposit of Microorganisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement, such as that required under 35 U.S.C. §112.

It is to be understood that the present invention is not limited to cultivation of the particular strain Bp3714-39. Rather, the present invention contemplates the cultivation of other organisms capable of producing compounds I-XI, such as mutants or variants of Bp3714-39 that can be derived from this organism by known means such as X-ray irradiation, ultraviolet irradiation, treatment with chemical mutagens, phage exposure, antibiotic selection and the like.

The antibiotic compounds of the present invention may be biosynthesized by various microorganisms. Microorganisms that may synthesize the compounds of the present invention include but are not limited to bacteria of the order Actinomycetales, also referred to as actinomycetes. Non-limiting examples of members belonging to the genera of actinomycetes include *Nocardia, Geodermatophilus, Actinoplanes, Micromonospora, Nocardioides, Saccharothrix, Amycolatopsis, Kutzneria, Saccharomonospora, Saccharopolyspora, Salinospora, Kitasatospora, Streptomyces, Microbispora, Streptosporangium*, and *Actinomadura*. The taxonomy of actinomycetes is complex and reference is made to Goodfellow, *Suprageneric Classification of Actinomycetes* (1989); *Bergey's Manual of Systematic Bacteriology*, Vol. 4 (Williams and Wilkins, Baltimore, pp. 2322 2339); and to Embley and Stackebrandt, "*The molecular phylogeny and systematics of the actinomycetes*," Annu. Rev. Microbiol. (1994) 48:257 289, each of which is hereby incorporated by reference in its entirety, for genera that may synthesize the compounds of the invention.

The compounds of structural formulas I to XI are produced by the aerobic fermentation of a suitable medium under controlled conditions via inoculation with a culture of the eubacterium *Nonomuraea* sp. The suitable medium is preferably aqueous and contains sources of assimilable carbon, nitrogen, and inorganic salts.

Suitable media include, without limitation, the growth media provided below in examples 1 and 2. The fermentation is conducted for about 2 to about 8 days at temperatures ranging from about 10° C. to about 40° C.; however for optimum results it is preferred to conduct the fermentation at about 30° C. The pH of the nutrient medium during the fermentation can be about 6.0 to about 9.0.

The culture media inoculated with the antibiotic compound producing microorganisms may be incubated under aerobic conditions using, for example, a rotary shaker or a stirred tank fermentor Aeration may be achieved by the injection of air, oxygen or an appropriate gaseous mixture to the inoculated culture media during incubation. As soon as a sufficient amount of the antibiotic compounds have accumulated, they may be concentrated and isolated from the culture in conventional and usual manner, for, example by extraction- and chromatographic methods, precipitation or crystallization, and/or in a manner disclosed herein. As an example for extraction, the culture can be mixed and stirred with a suitable organic solvent such as n-butanol, ethyl acetate, cyclohexane, n-hexane, toluene, n-butyl acetate or 4-methyl-2-pentanone, the antibiotic compounds in the organic layer can be recovered by removal of the solvent under reduced pressure. The resulting residue can optionally be reconstituted with for example water, ethanol, methanol or a mixture thereof, and re-extracted with a suitable organic solvent such as hexane, carbon tetrachloride, methylene chloride, dichloromethane or a mixture thereof. Following removal of the solvent, the compounds may be further purified for example by chromatographic methods. As an example for chromatography, stationary phases such as silica gel or aluminia oxide can be applied, with organic eluting solvents or mixtures thereof, including ethers, ketones, esters, halogenated hydrocarbons or alcohols, or reversed-phase chromatography on modified silica gel having various functional groups and eluting with organic solvents or aqueous mixtures thereof, like acetonitrile, methanol or tetrahydrofuran at different pH. Another example is partition-chromatography, for example in the solid-liquid or in the liquid-liquid mode. Also size exclusion chromatography may be applied, for example using Sephadex LH-20 (Sigma-Aldrich) and eluting with different solvents, preferably with alcohols.

As it is usual in this field, the production as well as the recovery and purification process may be monitored by a variety of analytical methods, including bioassays, TLC, HPLC or a combination thereof, and applying different detection methods, for TLC typically UV light, iodine vapor or spraying coloring reagents, for HPLC typically UV light, mass sensitive or light scattering methods. For example a HPLC technique is represented by using a reversed-phase column with a functionalized silica gel and applying an eluent which is a linear gradient mixture of a polar water miscible solvent and water at a specific pH, and a detection method with UV light at different wavelengths and a mass sensitive detector.

The antibiotic compound biosynthesized by microorganisms may optionally be subjected to random and/or directed chemical modifications to form compounds that are derivatives or structural analogs. Such derivatives or structural analogs having similar functional activities are within the scope of the present invention. Antibiotic compounds may optionally be modified using methods known in the art and described herein. Preferred synthetic antibiotic compounds include those selected from the group consisting of formulas XII to XXII and prepared as described herein.

Unless otherwise indicated, all numbers expressing quantities of ingredients, properties such as molecular weight, reaction conditions, $IC_{50}$ and so forth used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLE 1

Production of Compound I

Media Composition

| Seed medium | |
|---|---|
| Substance | Concentration [g/l] |
| Agar | 1 |
| Trace solution | 1 Ml |
| Glycerol | 7.5 |
| NaCl | 0.05 |
| $CaCO_3$ | 0.05 |
| $KH_2PO_4$ | 0.25 |
| $K_2HPO_4$ | 0.5 |
| $MgSO_4 \times 7\ H_2O$ | 0.1 |
| Yeast Extract | 1.35 |
| N-Z Amine A | 2.5 |
| Malt extract | 5.85 |
| L(-)Asparagine $\times$ 1 $H_2O$ | 1 |
| Soy protein | 2.5 |
| Starch | 7.5 |
| Glucose | 7.5 |
| Adjust to pH 7 | |

| Production medium A | |
|---|---|
| Substance | Concentration [g/l] |
| Agar | 1 |
| Trace solution | 1 mL |
| Glycerol | 7.5 |
| NaCl | 0.05 |
| $CaCO_3$ | 0.05 |
| $KH_2PO_4$ | 0.25 |
| $K_2HPO_4$ | 0.5 |
| $MgSO_4 \times 7\ H_2O$ | 0.1 |
| Yeast Extract | 1.35 |
| N-Z Amine A | 2.5 |
| Malt extract | 5.85 |
| L(-)Asparagine $\times$ 1 $H_2O$ | 1.0 |
| Soy protein | 2.5 |
| Starch | 7.5 |
| Glucose | 7.5 |
| Antifoam emulsion | 0.2 mL |
| Adjust to pH 7 | |

| Trace solution | |
|---|---|
| Substance | Concentration [g/l] |
| $ZnSO_4 \times 7\ H_2O$ | 4 |
| Boric acid $H_3BO_3$ | 0.1 |
| $FeSO_4 \times 7\ H_2O$ | 5 |
| KJ | 0.05 |
| $CoCl_2 \times 6\ H_2O$ | 2 |
| $CuSO_4 \times 5\ H_2O$ | 0.2 |

-continued

| Trace solution | |
|---|---|
| Substance | Concentration [g/l] |
| $MnCl_2 \times 4 H_2O$ | 2 |
| $H_2SO_4$ 95-97% | 1 mL |

A frozen suspension (1.5 mL) of a *Nonomuraea* sp. strain Bp3714-39 is inoculated into a two liter non-baffled shake flask containing 500 mL of seed medium. The flask is incubated for 3 days at 30° C. on a rotary shaker at 200 rpm and with 50 mm amplitude. The second seed stage is developed by inoculating 40 mL each, of the first stage seed into eight two liter non-baffled shake flasks each containing 500 mL of seed medium. The flask is incubated for 2 days at 30° C. on a rotary shaker at 200 rpm and with 50 mm amplitude. A third seed stage is developed by inoculating 4 liters each, of the second stage seed into two 150 liter scale stirred tank fermentors containing each 100 liters of seed medium. The 150 liter scale fermentors are operated for 3 days with the following parameters: Temperature=30° C., agitation=80 rpm, airflow=25 slpm, and pressure=0.5 bar. Excess foam formation is prevented by controlled addition of silicon oil-based antifoam agent. pH is monitored but not controlled.

A 5500 liter scale stirred tank fermentor containing 3500 liters of production medium A is inoculated with 200 liters from the third seed stage. Operating parameters of the 5500 liter scale fermentor are: Temperature=30° C., airflow=1050 slpm, and pressure=0.5 bar. Agitation is controlled at 60 rpm and, after 44 hours, increased to 80 rpm. Excess foam formation is prevented by controlled addition of silicon oil-based antifoam agent. pH is monitored but not controlled. The fermentor containing 3500 liters of broth is harvested after 5 days of incubation.

Isolation of Compound I

3500 L fermentation broth are harvested and extracted over night in a stirred tank by addition of 3900 L of ethyl acetate. As the pH of the fermentation broth is neutral at harvest (pH 7-8) there was no need to adjust the pH before extraction. During extraction the mixture is passed for 2 hours through a continuous Dispax® reactor (Jahnke & Kunkel, Germany) for maximum sheer force and optimal mixing. After separating the two phases on a continuous Westfalia separator SA20 (Westfalia Separator AG, Oelde, Germany) the ethyl acetate phase is concentrated to a volume of 30 liters by evaporation under reduced pressure. During evaporation a precipitate is formed which is separated by filtration. The precipitate had a dry weight of 197 g 4 g of the precipitate obtained from the extraction of the culture broth according to the procedure described above is dissolved in 20 ml Dioxane/water 95:5 and filtered to remove insoluble ingredients. The filtrate is concentrated under reduced pressure in the presence of 8 g diatome 8 (Isolute®, International Sorbent Technology Ltd., Hengoed Mid Glam, UK) The obtained powder is applied to a chromatographic column containing 180 g silica gel (0.040-0.063 mm, column size 5×25 cm) prepared in dichloromethane/methanol/acetic acid 90:10:0.5. The column is developed with a mixture of dichloromethane/methanol/acetic acid 90:10:0.5 at a flow rate of 35 mL/min. Fractions of 30 mL are collected, which are analyzed by HPLC. To the pooled fractions containing compound 120 mL Isopropanol is added and concentrated under reduced pressure until the compound precipitates from the remaining Isopropanol. After separating of the solvent from the precipitate through centrifugation the residue is dried under reduced pressure yielding in 800 mg semi-purified compound I.

For further purification the semi-purified material is dissolved in small volume of dioxane/water 95/5 and charged to a silica gel column, which is prepared and eluted under the same conditions as described for the first chromatographic step. The work up of the pooled fraction is identical to the work up of the first chromatographic step. After repetition of the second chromatographic step 61 mg compound I is obtained.

Physical Data of Compound I

IR (KBr pellet): 3380, 3114, 2972, 2928, 1664, 1533, 1516, 1417, 1312, 1230, 1174, 1103, 1063, 1024, 989, 934, 809, 756, 704, 600 cm$^{-1}$ FT-MS (9.4 T APEX-III): Found: 1339.21225; calc. for $C_{69}H_{60}N_{14}O_{12}S_6$+H, 1339.21296;

Found 1361.19419, calc. for $C_{59}H_{50}N_{14}O_{12}S_6$+Na; 1361.19491

$^1$H NMR (600 MHz) d$_6$-DMSO $\delta_H$: 0.94 (3H, d, J=7.3 Hz), 1.96 (2H, m), 2.55 (1H, m), 2.63 (1H, m), 2.69 (3H, s), 2.73 (1H, m), 2.76 (1H, m), 3.11 (1H, m), 3.21 (1H, m), 4.88 (1H, m), 5.19 (2H, m), 5.43 (1H, m), 5.47 (1H, m), 5.79 (1H, s), 5.82 (1H, s), 6.13 (1H, s), 6.35 (1H, broad), 6.47 (1H, s), 6.64 (2H, d, J=8.1 Hz), 6.81 (1H, s), 6.95 (2H, d, J=8.1 Hz), 7.04 (2H, m), 7.23 (3H, m), 7.32 (1H, s), 7.47 (1H, s), 7.72 (1H, d, J=8.1 Hz), 8.10 (1H, s), 8.16 (1H, s), 8.33 (1H, d, J=8.1 Hz), 8.47 (1H, d, J=8.1 Hz), 8.49 (1H, s), 8.63 (1H, s), 8.68 (1H, d, J=5.9 Hz), 8.99 (1H, d, J=7.3 hz), 9.07 (1H, d, broad), 9.25 (1H, s, broad), 9.59 (1H, s), 10.12 (1H, s); (signal of acidic proton of carboxylic acid not visible).

$^{13}$C NMR (150 MHz) d$_6$-DMSO $\delta_C$: 12.03, CH$_3$; 12.55, CH$_3$; 37.98, CH$_2$; 38.31, CH$_2$; 40.16, CH; 44.48, CH$_2$; 48.97, CH; 52.96, CH; 53.23, CH; 55.55, CH; 57.32, CH; 71.63, CH; 104.90, CH$_2$; 108.36, CH$_2$ (broad); 115.07, 2×CH; 116.26, CH; 118.66, CH; 123.03, CH; 125.39, CH; 126.28, 2×CH; 126.79, CH; 127.03, C$_q$; 127.31, CH; 127.63, 2×CH; 128.42, C$_q$; 128.75, CH; 129.95, 2×CH; 134.72, C$_q$; 135.20, C$_q$; 140.07, C$_q$; 140.17, C$_q$; 140.96, CH; 141.55, C$_q$; 147.15, C$_q$; 147.20, C$_q$; 149.50, C$_q$; 149.91, C$_q$; 150.27, C$_q$; 150.68, C$_q$; 152.99, C$_q$; 155.84, C$_q$; 158.85, C$_q$; 159.21, C$_q$; 160.00, C$_q$; 160.54, C$_q$; 161.42, C$_q$; 161.75, C$_q$; 164.25, C$_q$; 164.71, C$_q$; 166.43, C$_q$; 167.59, C$_q$; 168.23; C$_q$; 171.39, C$_q$; 171.64, C$_q$; 173.06, C$_q$.

EXAMPLE 2

Production of Compounds II, III, IV, V, VI, VII, VIII, IX

Media Composition
Seed medium and trace solution is the same as in example 1.

| Production medium B | |
|---|---|
| Substance | Concentration [g/l] |
| Soyflour, de-fatted | 20 |
| D(−)-Mannitol | 20 |
| Trace solution | 1 mL |
| Adjust to pH 7.5 | |

A frozen suspension (1.5 mL) of a *Nonomuraea* sp. strain Bp3714-39 is inoculated into a 500 mL non-baffled shake flask containing 50 mL of seed medium. The flask is incubated for 5 days at 28° C. on a rotary shaker at 200 rpm and with 50 mm amplitude. The second seed stage is developed by inoculating 5 mL each, of the first stage seed into eight 2-liter non-baffled shake flasks each containing 500 mL of seed medium. The flasks are incubated for 3 days at 28° C. on a rotary shaker at 200 rpm and with 50 mm amplitude.

A 150 liter scale stirred tank fermentor containing 100 liters of production medium B is inoculated with 4 liters from the second seed stage. Operating parameters of the 150 liter scale fermentor are: Temperature=28° C., airflow=50 slpm, and pressure=0.5 bar. Agitation is controlled at 80 rpm. Excess foam formation is prevented by controlled addition of silicon oil-based antifoam agent. pH is monitored but not controlled. The fermentor containing 100 liters of broth is harvested after 5 days of incubation. Before harvesting the pH of the fermentation broth was set to pH 4.5 by addition of 300 ml of 4N $H_2SO_4$.

Isolation of Compounds II, III, IV, V, VI, VII, VIII, IX

100 L fermentation broth are harvested and extracted in a stirred tank by addition of 200 liters ethyl acetate and passing for 1 hour through a continuous Dispax® reactor (Jahnke&Kunkel, Germany) for maximum sheer force and optimal mixing. Afterwards the two phases are separated and the organic phase containing the extracted metabolites is evaporated under reduced pressure until dry, resulting in 98 g dry extract. For de-fatting the extract is solved in 1 liter MeOH/$H_2O$ 9/1 and extracted 3 times with 1 liter cyclohexane. The hexane phase containing the fatty compounds is discarded whereas the MeOH phase is evaporated under reduced pressure with the addition of 1 liter water. The water phase is re-extracted with 3 liters ethyl acetate. After separation, the organic phase is evaporated until dry, resulting in 9.3 g of de-fatted extract.

The extract is dissolved in methanol and applied to a column containing Sephadex LH20 prepared in methanol. The column is eluted with Methanol. Fractions containing the compounds are further purified using reversed phase chromatography with water and acetonitrile or methanol as solvent system. To the solvents 0.01% trifluoroacetic acid or 0.1% orthophosphoric acid are added. Fractions containing the compounds are diluted with the same volume of water, adsorbed on Oasis HLB column (Waters Corporation, USA) and eluted with Methanol and evaporated to dryness.

The purification yielded in 12 mg compound II, 1 mg compound III, 4 mg compound IV), 2 mg compound V, 0.5 mg compound VI, 2 mg compound VII, 8 mg compound VIII and 5 mg compound IX.

Physical Data of Compound II
FT-MS (9.4 T APEX-III): Found: 1339.20912; calc. for $C_{59}H_{52}N_{14}O_{12}S_6$—H, 1339.21406.
$^1$H NMR (600 MHz) $d_6$-DMSO $\delta_H$: 0.75 (3H, d, J=7.0 Hz), 1.09 (3H, d, J=7.0 Hz), 2.02 (1H, m, broad), 2.07 (1H, m), 2.64 (1H, m), 2.68 (3H, s), 2.76 (1H, m), 3.18 (1H, m), 3.82 (1H, m), 4.81 (1H, m), 4.5-5.0 (1H, broad), 5.21 (2H, m), 5.43 (1H, m), 5.47 (1H, m), 5.82 (1H, s), 5.86 (1H, s), 6.13 (1H, s), 6.33 (1H, broad), 6.48 (1H, s), 6.65 (2H, d, J=8.4 Hz), 6.82 (1H, s), 6.97 (2H, d, J=8.4 Hz), 7.08 (2H, m), 7.24 (3H, m), 7.33 (1H, s), 7.52 (1H, s), 7.74 (1H, broad), 8.02 (1H, s), 8.16 (1H, s), 8.34 (1H, d, J=8.1 Hz), 8.47 (1H, d, J=8.1 Hz), 8.51 (1H, s), 8.63 (1H, s), 8.66 (1H, d, J=6.6 Hz), 9.00 (2H, m), 9.25 (1H, broad), 9.59 (1H, s), 10.11 (1H, s); (signal of acidic proton of carboxylic acid not visible).

Physical Data of Compound III
FT-MS (9.4 T APEX-III): Found: 1379.20082; calc. for $C_{59}H_{52}N_{14}O_{13}S_6$+Na: 1379.20550.
$^1$H NMR (600 MHz) $d_6$-DMSO $\delta_H$: due to low amounts no complete assignment Physical Data of Compound IV
FT-MS (9.4 T APEX-III): Found: 1337.20422; calc. for $C_{59}H_{50}N_{14}O_{12}S_6$—H, 1337.19841.
$^1$H NMR (600 MHz) $d_6$-DMSO $\delta_H$: 0.97 (3H, d, J=7.0 Hz), 1.95 (1H, m), 2.28 (3H, s), 2.61 (1H, m), 2.65 (3H, s), 2.67 (1H, m), 3.09 (1H, m), 3.19 (1H, m), 4.75 (1H, m), 5.18 (1H, m), 5.26 (1H, m), 5.38 (1H, m), 5.43 (1H, m), 5.83 (2H, s), 6.04 (1H, s), 6.28 (1H, d, J=3.7 Hz), 6.44 (1H, s), 6.59 (2H, d, J=8.1 Hz), 6.78 (1H, s), 6.88 (2H, d, J=8.1 Hz), 7.03 (2H, m), 7.19 (3H, m), 7.27 (1H, s), 7.51 (1H, s), 7.65 (1H, d, J=9.5 Hz), 8.09 (1H, s), 8.14 (1H, s), 8.35 (1H, d, J=8.1 Hz), 8.51 (2H, s+d, J=8.1 Hz), 8.59 (1H, d, J=8.1 Hz), 8.66 (1H, s), 8.90 (1H, d, J=8.1 Hz), 8.96 (1H, d, J=5.9 Hz), 9.15 (1H, s), 9.59 (1H, s), 10.09 (1H, s), 13.33 (1H, broad).

Physical Data of Compound V
FT-MS (9.4 T APEX-III): Found: 1377.18771; calc. for $C_{59}H_{60}N_{14}O_{13}S_6$+Na: 1377.18983,
Found: 1353.19568; calc. for $C_{59}H_{50}N_{14}O_{13}S_6$—H, 1353.19278.
$^1$H NMR (600 MHz) $d_6$-DMSO $\delta_H$: 0.95 (3H, d, J=7.0 Hz), 1.89 (1H, broad), 2.59 (1H, m), 2.66 (3H, s), 2.68 (1H, m), 3.10 (1H, m), 3.33 (1H, m), 4.33 (1H, m), 4.38 (1H, m), 4.74 (1H, m), 5.17 (1H, m), 5.27 (1H, m), 5.36 (1H, m), 5.40 (1H, m), 5.44 (1H, m), 5.83 (1H, s), 5.84 (1H, s), 6.04 (1H, s), 6.32 (1H, d, J=3.5 Hz), 6.45 (1H, s), 6.57 (2H, d, J=8.2 Hz), 6.80 (1H, s), 6.86 (2H, d, J=8.2 Hz), 7.01 (2H, m), 7.20 (3H, m), 7.28 (1H, s), 7.50 (1H, s), 7.60 (1H, d, J=8.8 Hz), 8.15 (1H, s), 8.16 (1H, s), 8.36 (1H, d, J=8.1 Hz), 8.53 (2H, s+d, J=8.1 Hz), 8.61 (1H, d, J=6.0 Hz), 8.68 (1H, s), 8.91 (1H, d, J=7.8 Hz), 8.98 (1H, d, J=5.9 Hz), 9.16 (1H, s), 9.63 (1H, s), 10.11 (1H, s), 13.38 (1H, broad).

Physical Data of Compound VI
FT-MS (9.4. T APEX-III): Found: 1397.15629; calc. for $C_{69}H_{61}ClN_{14}O_{12}S_6$+Na: 1397.17159. Found: 1373.17348; calc. for $C_{59}H_{51}N_{14}O_{12}S_6$—H, 1373.17509.
$^1$H NMR (600 MHz) $d_6$-DMSO $\delta_H$: 0.81 (3H, d, J=6.6 Hz), 2.10 (1H, broad), 2.25 (1H, m), 2.66 (3H, s), 2.70 (1H, m), 2.74 (1H, m), 3.16 (1H, m), 3.65 (1H, m), 3.77 (1H, m), 3.80 (1H, m), 4.81 (1H, m), 5.23 (1H, m), 5.39 (1H, m), 5.41 (1H, m), 5.45 (1H, m), 5.48 (1H, broad), 5.76 (1H, s), 5.77 (1H, s), 6.04 (1H, s), 6.26 (1H, s), 6.44 (1H, s), 6.65 (2H, d, J=8.2 Hz), 6.80 (1H, s), 6.98 (2H, d, J=8.2 Hz), 7.10 (2H, m), 7.23 (3H, m), 7.31 (1H, s), 7.55 (1H, s), 7.79 (1H, d, J=7.3 Hz), 8.00 (1H, s), 8.14 (1H, s), 8.37 (1H, d, J=8.1 Hz), 8.51 (1H, d, J=8.1 Hz), 8.54 (1H, s), 8.58 (1H, d, J=6.6 Hz), 8.67 (1H, s), 8.90 (1H, broad), 9.00 (1H, d, J=7.3 Hz), 9.2 (1H, s, broad), 9.68 (1H, s), 10.11 (1H, s); (signal of acidic proton of carboxylic acid not visible).

Physical Data of Compound VII
FT-MS (9.4 T APEX-III): Found: 1323.21872; calc. for $C_{59}H_{52}N_{14}O_{11}S_6$—H, 1323.21915.
$^1$H NMR (600 MHz) $d_6$-DMSO $\delta_H$: 0.85 (3H, d, J=6.7 Hz), 0.92 (3H, t, J=7.3 Hz), 1.32 (1H, m), 1.63 (1H, m), 1.93 (2H, m), 2.59 (1H, m), 2.66 (3H, s), 2.70 (1H, m), 3.14 (1H, m), 4.83 (1H, m), 4.88 (1H, m), 5.16 (1H, m), 5.40 (1H, m), 5.44 (1H, m), 5.95 (1H, s), 6.31 (1H, s), 6.32 (1H, s), 6.42 (1H, s), 6.53 (1H, s), 6.60 (2H, d, J=8.1 Hz), 6.81 (1H, s), 6.91 (2H, d, J=8.1 Hz), 7.02 (2H, m), 7.21 (3H, m), 7.27 (1H, s), 7.49 (1H, s), 7.63 (1H, d, J=7.0 Hz), 8.09 (1H, s), 8.14 (1H, s), 8.38 (1H, d, J=8.1 Hz), 8.53 (2H, s+d, J=8.1 Hz), 8.64 (1H, d, J=5.7 Hz), 8.68 (1H, s), 8.90 (1H, d, J=7.6 Hz), 8.94 (1H, broad), 9.18 (1H, s), 9.97 (1H, broad), 10.14 (1H, s), (signals of acidic proton of carboxylic acid not visible).

Physical Data of Compound VIII
FT-MS (9.4 T APEX-III): Found: 1307.21868; calc. for $C_{59}H_{52}N_{14}O_{10}S_6$—H, 1307.22432.
$^1$H NMR (600 MHz) $d_6$-DMSO $\delta_H$: 0.88 (3H, d, J=6.7 Hz), 0.93 (3H, t, J=7.3 Hz), 1.32 (1H, m), 1.62 (1H, m), 1.99 (1H, m), 2.11 (1H, m), 2.64 (3H, s), 2.76 (1H, m), 2.79 (1H, m), 3.22 (2H, m), 3.38 (1H, m), 4.90 (1H, m), 4.94 (1H, m), 5.29 (1H, m), 5.54 (1H, q, J=6.7 Hz), 5.84 (1H, s), 5.85 (1H, s), 6.04 (1H, s), 6.45 (1H, s), 6.66 (2H, d, J=8.2 Hz), 6.83 (1H, s), 7.07 (2H, d, J=8.2 Hz), 7.10 (2H, d, J=7.2 Hz), 7.19 (1H, t, J=7.0 Hz), 7.24 (2H, t, J=7.0 Hz), 7.32 (1H, s), 7.54 (1H, s), 7.89 (1H, d, J=9.6 Hz), 8.12 (1H, s), 8.21 (1H, s), 8.37 (1H, d, J=8.1 Hz), 8.53 (2H, s+d, J=8.1 Hz), 8.68 (1H, s), 8.84 (1H, d, J=7.2 Hz), 8.86 (1H, d, J=8.1 Hz), 8.93 (1H, d, J=5.8 Hz), 9.21 (1H, m), 9.62 (1H, s), 10.11 (1H, s); 13.37 (1H, broad).

Physical Data of Compound Ix

FT-MS (9.4 T APEX-III): Found: 1337.19576; calc. for $C_{59}H_{50}N_{14}O_{12}S_6$—H, 1337.19841.

$^1$H NMR (600 MHz) d$_6$-DMSO δ$_H$: 1.12 (3H, d, J=6.2 Hz), 1.75 (1H, m), 1.89 (1H, m), 2.12 (1H, m), 2.57 (2H, m), 2.62 (1H, m), 2.68 (3H, s), 3.29 (1H, m), 4.62 (1H, d, J=~9.5 Hz), 5.1 (1H, m), 5.18 (1H, m), 5.34 (1H, d, J=4.8 Hz), 5.45 (1H, m), 5.79 (1H, d, J=3.7 Hz), 5.87 (2H, s), 6.06 (1H, s), 6.36 (1H, broad), 6.44 (1H, s), 6.55 (1H, broad), 6.57 (2H, d, J=8.1 Hz), 6.64 (1H, s), 6.84 (2H, d, J=8.1 Hz), 6.95 (2H, m), 7.13 (1H, s), 7.21 (3H, m), 7.35 (1H, s), 7.45 (1H, d, J=9.9 Hz), 8.16 (1H, s), 8.21 (1H, s), 8.35 (1H, d, J=8.1 Hz), 8.52 (1H, d, J=8.5 Hz), 8.55 (1H, s), 8.62 (1H, d, J=5.9 Hz), 8.67 (1H, s), 8.84 (1H, d, J=7.7 Hz), 9.09 (1H, s), 9.55 (1H, s), 10.1 (1H, s), 13.16 (1H, broad)

EXAMPLE III

Isolation of Compounds X and XI

The fermentation and extractions conditions are identical to the conditions described in example I.

For isolation of compound X the precipitate is applied to a reversed phase column which is equilibrated with a mixture of 60% water and 40% acetonitrile. For eluting of the compound a gradient starting with 40% acetonitrile to 60% acetonitrile is applied. Fractions containing compound X are further purified on a reversed phase column using water and acetonitrile both containing 0.1% formic acid as eluent. Fractions containing compound X are concentrated under reduced pressure.

For isolation of compound XI the precipitate is applied to a normal phase column which is prepared in dichloromethane/methanol/formic acid 95:5:0.1. The compound is eluted using the same solvent system. Fractions containing XI are further purified using a reversed phase column with water acetonitrile both containing 0.1% formic acid as solvent. For chromatography a gradient starting with 30% acetonitrile to 60% acetonitrile is applied. Fractions containing compound XI are concentrated under reduced pressure.

Physical Data of Compound X

FT-MS (9.4 T APEX-III): Found: 1363.20993; calc. for $C_{69}H_{52}N_{14}O_{12}S_6$+Na: 1363.21060.

$^1$H NMR (600 MHz) d$_6$-DMSO δ$_H$: 0.91 (3H, d, J=6.5 Hz), 1.46 (1H, m), 1.79 (1H, m), 1.92 (1H, m), 2.19 (1H, m), 2.60 (1H, m), 2.69 (3H, s), 2.74 (1H, m), 3.17 (1H, m), 3.50 (1H, m), 3.57 (1H, m), 4.90 (1H, m), 4.96 (1H, m), 5.18 (1H, m), 5.42 (1H, m), 5.47 (1H, m), 5.79 (1H, s), 5.82 (1H, s), 6.12 (1H, s), 6.35 (1H, broad), 6.47 (1H, s), 6.63 (2H, d, J=8.2 Hz), 6.79 (1H, s), 6.94 (2H, d, J=8.2 Hz), 7.03 (2H, m), 7.23 (3H, m), 7.30 (1H, s), 7.46 (1H, s), 7.66 (1H, d, J=8.8 Hz), 8.11 (1H, s), 8.16 (1H, s), 8.35 (1H, d, J=8.1 Hz), 8.48 (1H, d, J=8.1 Hz), 8.50 (1H, s), 8.64 (1H, s), 8.68 (1H, d, J=5.2 Hz), 8.95 (1H, d, J=6.6 Hz), 9.00 (1H, d, J=5.9 Hz), 9.11 (1H, broad), 9.61 (1H, s), 10.12 (1H, s); (signals of one hydroxyl group and of acidic proton of carboxylic acid not visible.

Physical Data of Compound XI

FT-MS (9.4 T APEX-III): Found: 1379.19875; calc. for $C_{59}H_{52}N_{14}O_{13}S_6$+Na: 1379.20547;

Found: 1355.21523; calc. for $C_{59}H_{52}N_{14}O_{13}S_6$—H, 1355.20898.

$^1$H NMR (600 MHz) d$_6$-DMSO δ$_H$: 0.67 (3H, s, broad), 2.29 (1H, m), 2.58 (3H, s), 2.78 (1H, m), 2.84 (1H, m), 2.98 (1H, m), 3.08 (1H, m), 3.38 (1H, m, broad), 3.52 (1H, m, broad), 4.30 (1H, broad), 4.74 (1H, m), 4.90 (1H, broad), 4.99 (1H, m), 5.27 (1H, m), 5.32 (1H, m), 5.48 (1H, m), 5.74 (1H, s), 5.76 (1H, s), 6.00 (1H, s), 6.16 (1H, s), 6.43 (1H, s), 6.64 (2H, d, J=8.4 Hz), 6.87 (1H, s), 7.03 (2H, d, J=8.4 Hz), 7.19 (1H, m), 7.25 (4H, m), 7.40 (1H, s), 7.60 (1H, broad), 8.11 (2H, s+s, broad), 8.36 (1H, d, J=8.1 Hz), 8.43 (1H, d, J=7.3 Hz), 8.50 (1H, d, J=8.1 Hz), 8.51 (1H, m, broad), 8.52 (1H, s), 8.66 (1H, s), 8.89 (1H, d, J=8.0 Hz), 9.20 (1H, s), 9.69 (1H, s), 10.08 (1H, s), (signals of one NH2 group and of acidic proton of carboxylic acid not visible).

EXAMPLE IV

Production of Compounds XI through XXII

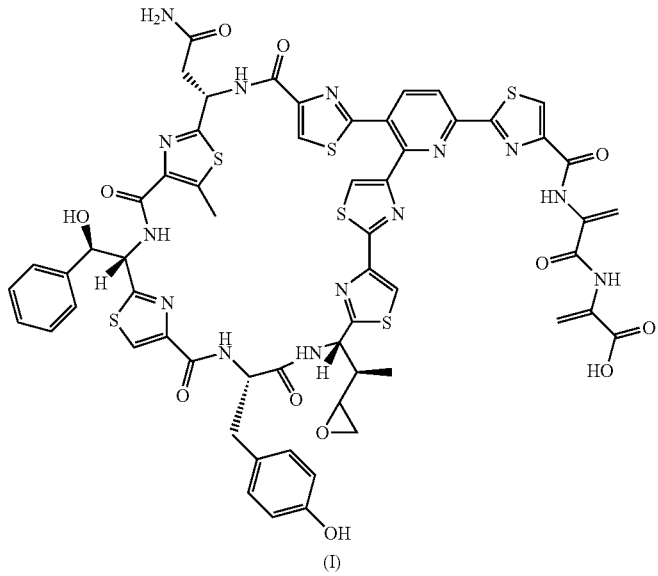

(I)

Reaction A

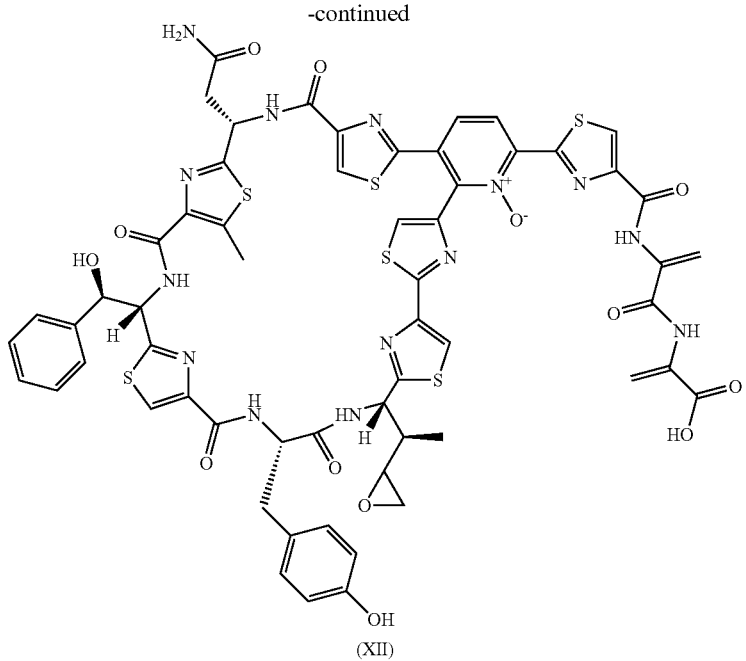

(XII)

The pyridine N-oxides (formulas XII through XXII) may be prepared through reaction A (above) by treatment of the freebase (e.g., I) with an oxidizing agent. This oxidation process is commonly recognized by those skilled in the art. The pyridine N-oxides may be useful intermediates for isolation, purification, and further chemical synthesis.

EXAMPLE V

Biological Activity

Using a CSLI standard MIC (minimum inhibitory concentration) test with the bacteria *Enterococcus faecalis, Enterococcus faecium* and *Staphylococcus aureus*, compounds I-XI demonstrate a minimum inhibitory concentration ranging from 0.0010 µg/mL to 64 µg/mL.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

We claim:
1. A compound selected from the group consisting of the formulas I-XI

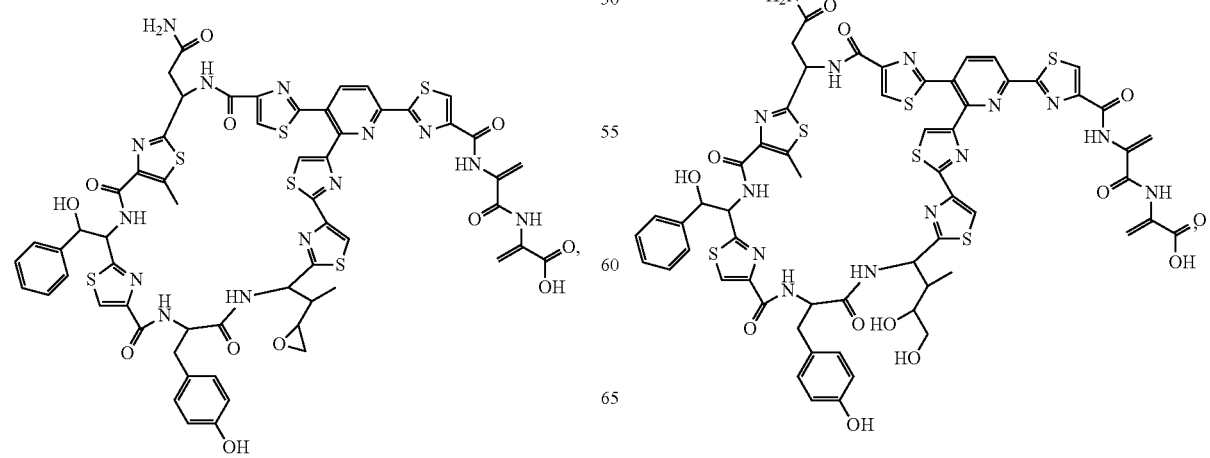

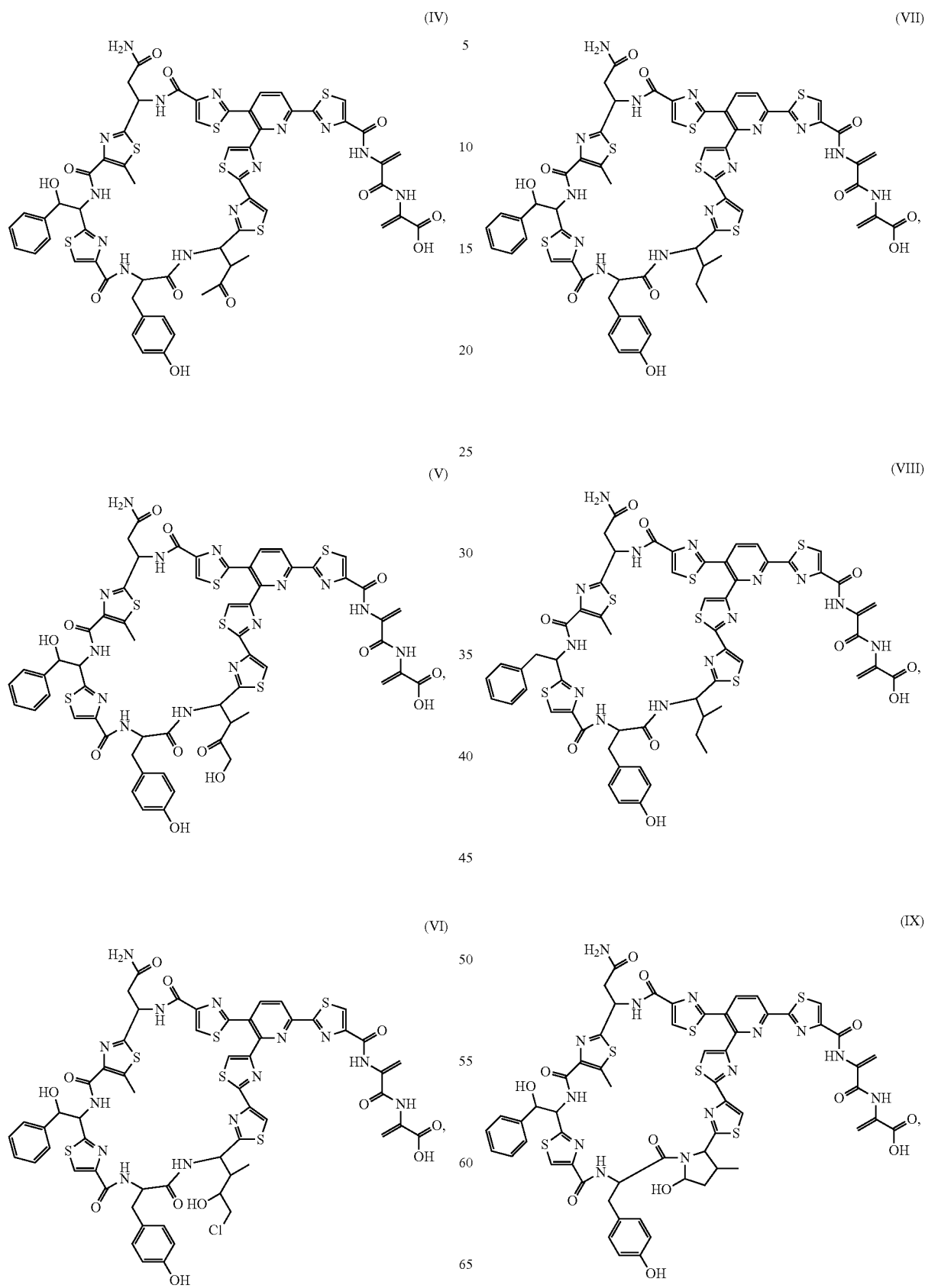

(X)
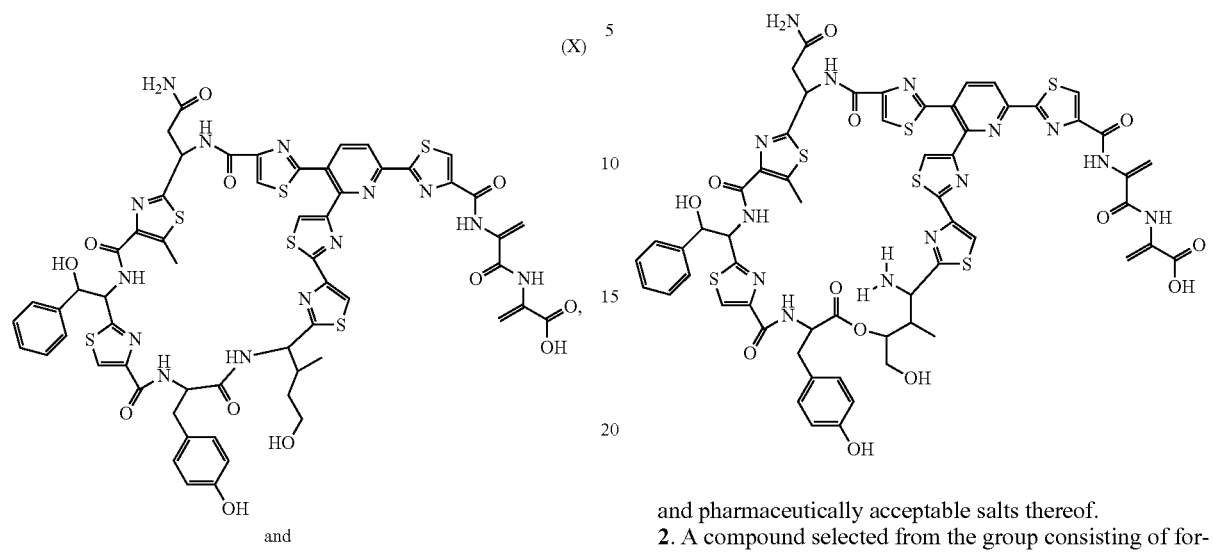
and
(XI)
and pharmaceutically acceptable salts thereof.
2. A compound selected from the group consisting of formulas XII-XXII
(XII)
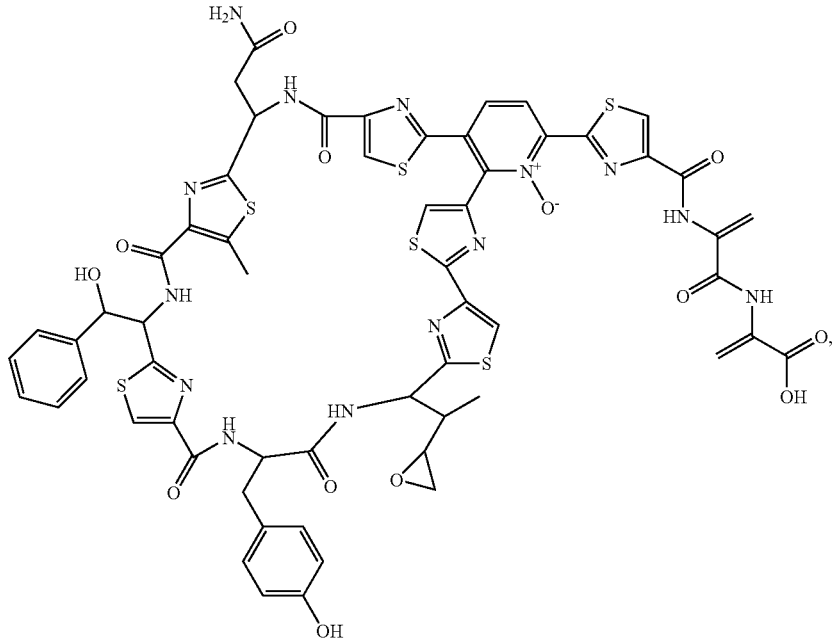

(XIII)
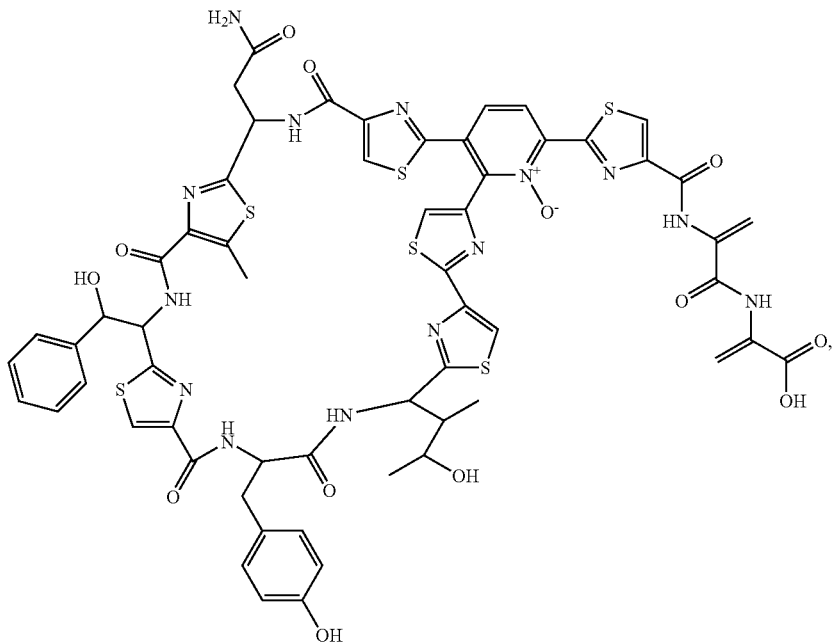
(XIV)
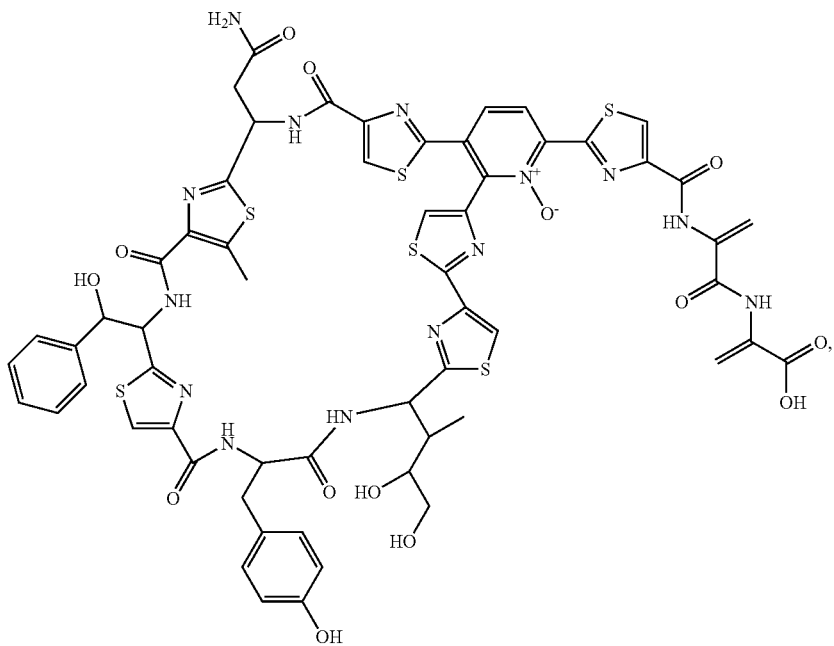

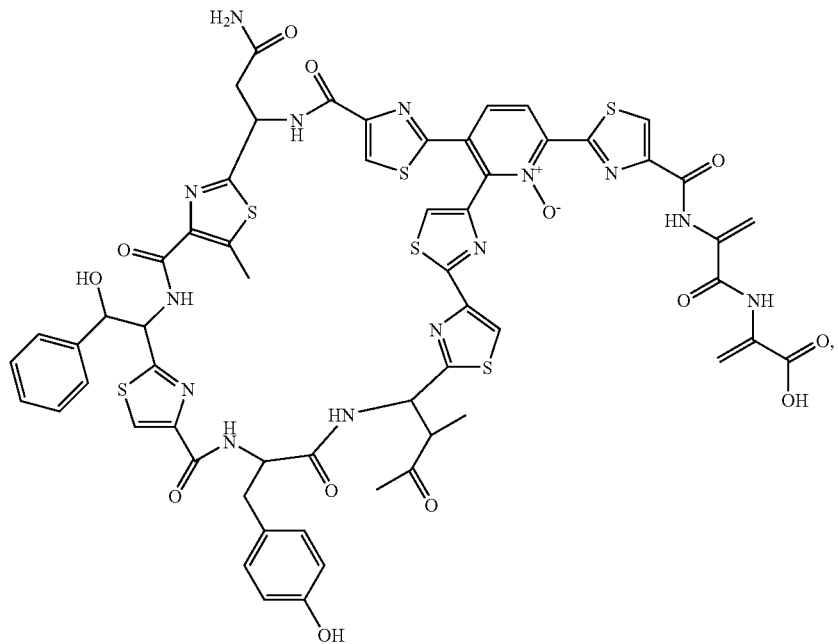
(XV)
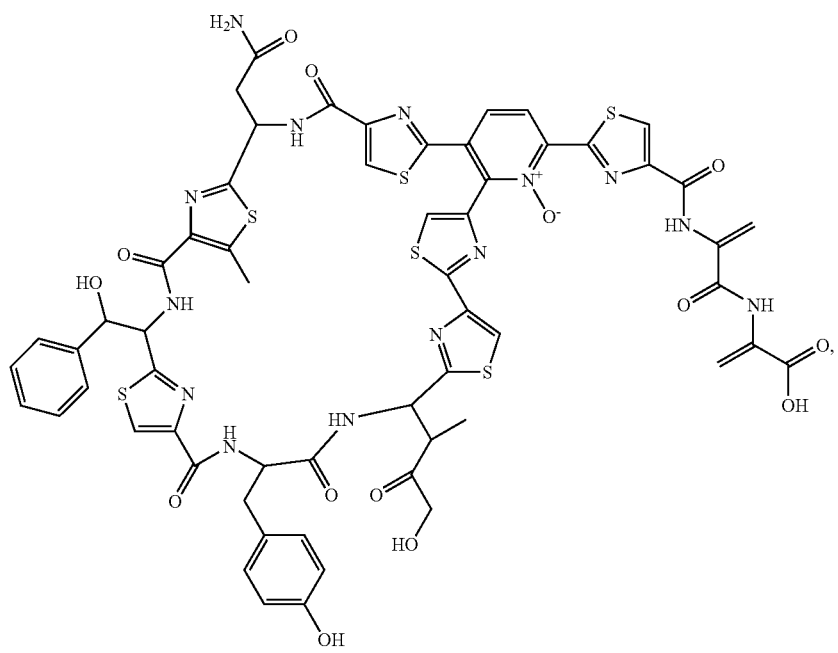
(XVI)

-continued
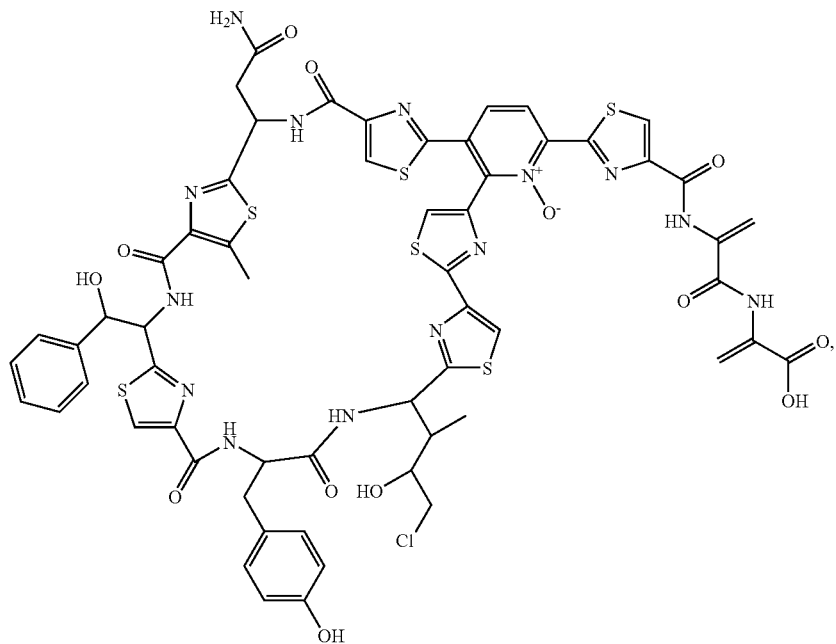
(XVII)
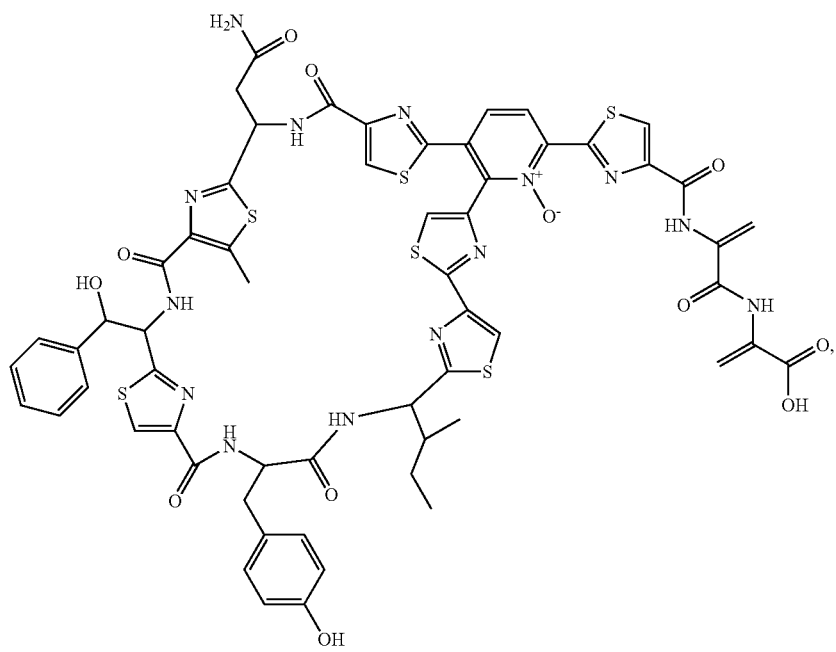
(XVIII)

-continued
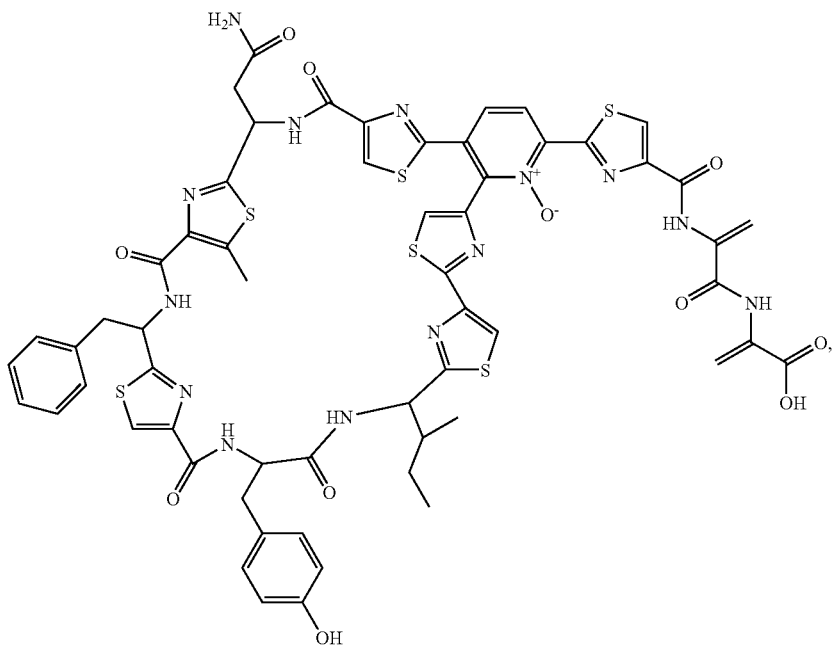
(XIX)
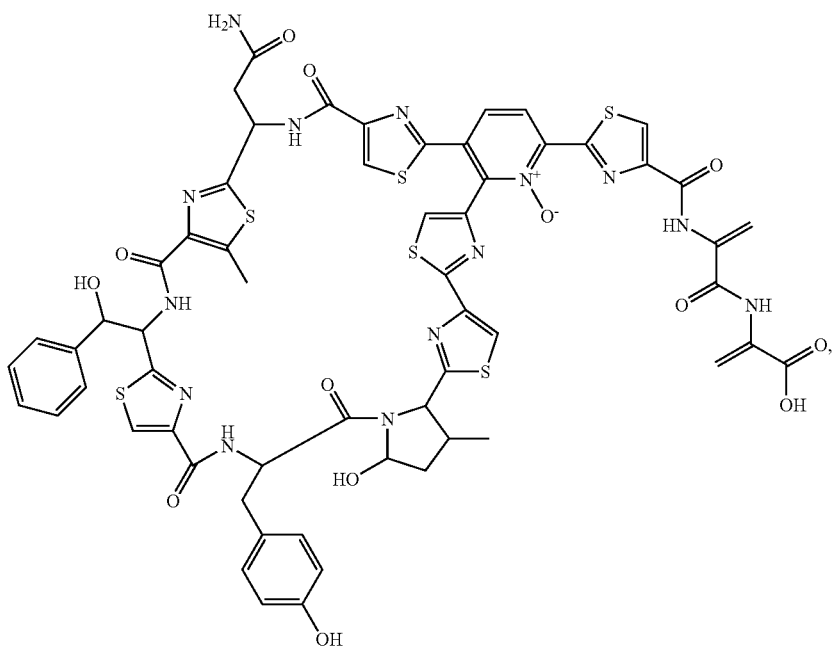
(XX)

-continued

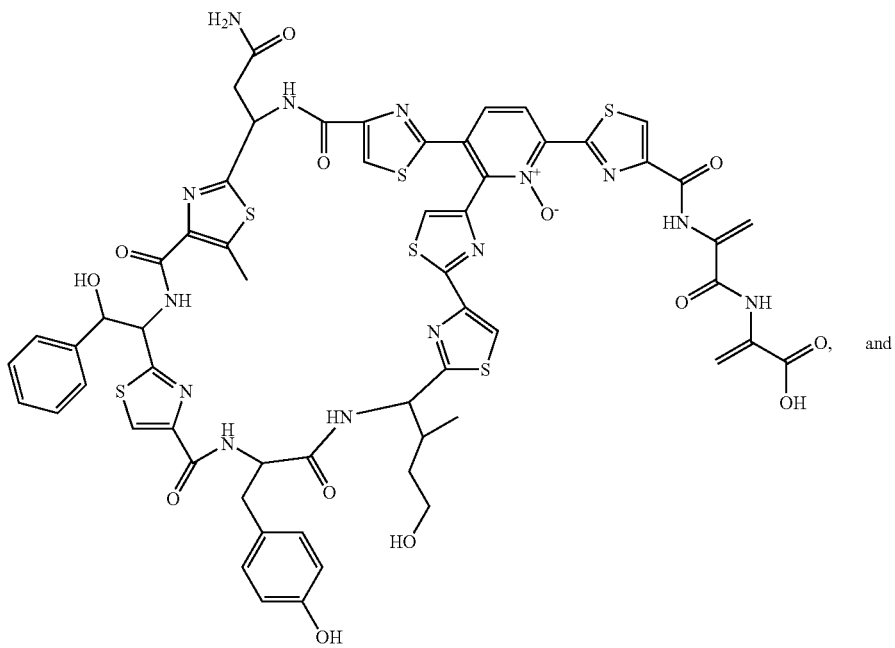

(XXI)

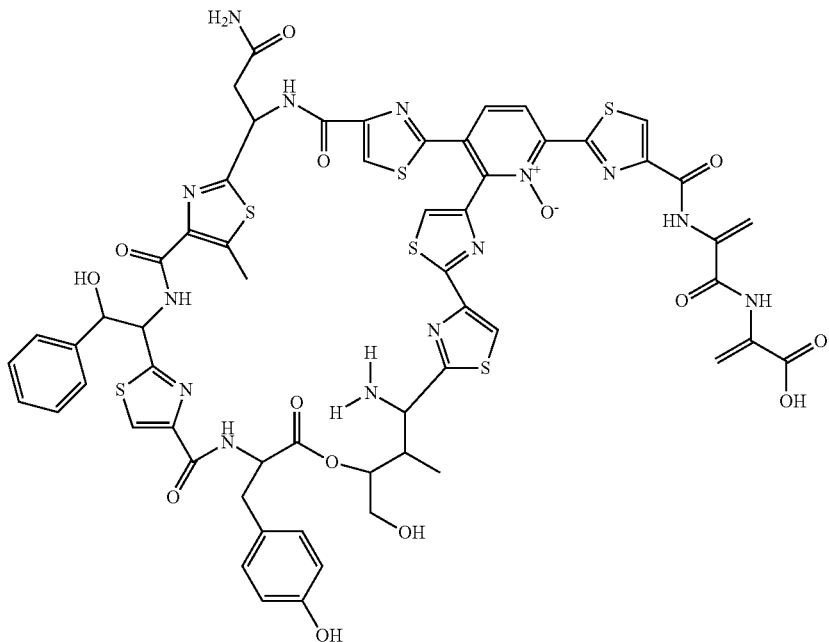

(XXII)

and pharmaceutically acceptable salts thereof.

3. A process for producing compounds I-XI cultivation of cultivating a strain of *Nonomuraea* sp Bp3714-39, using said strain in the presence of a suitable medium comprising at least one source of carbon atoms and at least on source of nitrogen atom to produce compounds I-XI.

4. The process of claim 3, wherein said cultivation occurs under aerobic conditions.

5. The process of claim 3, wherein said carbon source is selected from the group consisting of agar, corn steep liquor, fish oils, fructose, glucose, glycerol, lactose, malt extract, mannitol, mannose, meat extract, plant oils, saccarose, skim milk powder, starch, wheat extract and yeast extract, or said nitrogen source is selected from the group consisting of amino acid mixture, ammonium, asparagine, brain heart infusion, casein peptones, corn steep liquor, cysteine, meat peptones, nitrate, plant peptones, proline, serine, soy flour, soy protein, tyrosine, valine and yeast extract.

6. The process of claim 3, wherein said cultivation is carried out at a temperature from 18° C. to 40° C.

7. The process of claim 3 wherein said cultivation is carried out at a temperature from 28° C. to 32° C.

8. The process of claim 3, wherein said cultivation is carried out at pH from 6 to 9.

9. A method of treating, inhibiting or ameliorating bacterial infection in a subject, comprising administering to said subject a therapeutically effective amount of a compound selected from the group consisting of formulas I-XXII.

10. The method according to claim 9 wherein said compound inhibits a bacterial target affecting the lifecycle of bacteria.

11. The method of claim 10, wherein the bacterial target is EF-Tu.

12. The method of claim 10, wherein the compound inhibits protein synthesis in bacteria.

13. A method of treating a bacterial infection comprising administering to a subject in need thereof a therapeutically effective amount of compound selected from the group consisting of formulas I-XXII, or a pharmaceutically acceptable salt thereof, in combination with a therapeutically effective amount of at least one or more therapeutic agents or pharmaceutically acceptable salts thereof.

14. A method of treating acne or bacterial endocarditis in subject in need thereof comprising administering to the subject a pharmaceutically acceptable amount of a compound of formulas I-XXII.

* * * * *